(12) United States Patent
Ben Nun

(10) Patent No.: US 8,273,123 B2
(45) Date of Patent: Sep. 25, 2012

(54) UNITARY ACCOMMODATING INTRAOCULAR LENSES (AIOLS) AND DISCRETE BASE MEMBERS FOR USE THEREWITH

(75) Inventor: Joshua Ben Nun, D.N. Vitkin (IL)

(73) Assignee: Nulens Ltd., Herzliya (IL)

( * ) Notice: Subject to any disclaimer, the term of this patent is extended or adjusted under 35 U.S.C. 154(b) by 413 days.

(21) Appl. No.: 12/529,705

(22) PCT Filed: Mar. 5, 2008

(86) PCT No.: PCT/IL2008/000284
§ 371 (c)(1),
(2), (4) Date: Sep. 2, 2009

(87) PCT Pub. No.: WO2008/107882
PCT Pub. Date: Sep. 12, 2008

(65) Prior Publication Data
US 2010/0121444 A1    May 13, 2010

(30) Foreign Application Priority Data

Mar. 5, 2007  (IL) .......................................... 181710
Apr. 17, 2007  (IL) .......................................... 182604
Sep. 5, 2007  (IL) .......................................... 185740

(51) Int. Cl.
*A61F 2/16* (2006.01)
(52) U.S. Cl. ...................... 623/6.34; 623/6.22; 623/6.41
(58) Field of Classification Search .................. 623/6.34, 623/6.38–6.41, 6.43
See application file for complete search history.

(56) References Cited

U.S. PATENT DOCUMENTS
3,950,082 A    4/1976  Volk
(Continued)

FOREIGN PATENT DOCUMENTS
EP    0 156 472 A    10/1985
(Continued)

OTHER PUBLICATIONS

Notification of Transmittal of the International Preliminary Report on Patentability for PCT/IL2009/000728 filed Jul. 26, 2009 (having a priority date of Jul. 24, 2008).

(Continued)

*Primary Examiner* — David H Willse
*Assistant Examiner* — Tiffany Shipmon
(74) *Attorney, Agent, or Firm* — Morgan, Lewis & Bockius LLP

(57) ABSTRACT

Unitary accommodating intraocular lenses (AIOLs) including a haptics system for self-anchoring in a human eye's ciliary sulcus and a resiliently elastically compressible shape memory optical element having a continuously variable Diopter strength between a first Diopter strength in a non-compressed state and a second Diopter strength different than its first Diopter strength in a compressed state. The unitary AIOLS include an optical element with an exposed trailing surface and are intended to be used with a discrete base member for applying an axial compression force against the exposed trailing surface from a posterior direction. Some unitary AIOLs are intended to be used with either a purpose designed base member or a previously implanted standard in-the-bag IOL. Other unitary AIOLs are intended to be solely used with a purpose designed base member.

13 Claims, 28 Drawing Sheets

U.S. PATENT DOCUMENTS

| | | | |
|---|---|---|---|
| 4,122,556 A | 10/1978 | Poler | |
| 4,254,509 A | 3/1981 | Tennant | |
| 4,298,994 A | 11/1981 | Clayman | |
| 4,340,979 A | 7/1982 | Kelman | |
| 4,409,690 A | 10/1983 | Gess | |
| 4,409,691 A | 10/1983 | Levy | |
| 4,445,998 A | 5/1984 | Kanda et al. | |
| 4,446,581 A | 5/1984 | Blake | |
| 4,494,254 A | 1/1985 | Lopez | |
| 4,530,117 A | 7/1985 | Kelman | |
| RE31,963 E | 8/1985 | Kelman | |
| 4,556,998 A | 12/1985 | Siepser | |
| 4,575,374 A | 3/1986 | Anis | |
| 4,581,033 A | 4/1986 | Callahan | |
| 4,589,147 A | 5/1986 | Nevyas | |
| 4,591,358 A | 5/1986 | Kelman | |
| 4,615,701 A | 10/1986 | Woods | |
| 4,671,283 A | 6/1987 | Hoskin et al. | |
| 4,676,794 A | 6/1987 | Kelman | |
| 4,750,904 A | 6/1988 | Price, Jr. | |
| 4,808,181 A | 2/1989 | Kelman | |
| 4,842,601 A | 6/1989 | Smith | |
| RE33,039 E | 8/1989 | Arnott | |
| 4,865,601 A | 9/1989 | Caldwell et al. | |
| 4,888,012 A | 12/1989 | Horn et al. | |
| 4,892,543 A | 1/1990 | Turley | |
| 4,932,966 A | 6/1990 | Christie et al. | |
| 4,932,968 A | 6/1990 | Caldwell et al. | |
| 4,957,505 A | 9/1990 | McDonald | |
| 4,969,897 A | 11/1990 | Kalb | |
| 4,976,732 A | 12/1990 | Vorosmarthy | |
| 4,990,159 A | 2/1991 | Kraff | |
| 5,026,373 A | 6/1991 | Ray | |
| 5,078,742 A | 1/1992 | Dahan | |
| 5,171,268 A | 12/1992 | Ting et al. | |
| 5,176,701 A | 1/1993 | Dusek et al. | |
| 5,275,623 A | 1/1994 | Sarfarazi | |
| 5,282,851 A | 2/1994 | Jacob-LaBarre | |
| 5,288,293 A | 2/1994 | O'Donnell, Jr. | |
| 5,336,262 A | 8/1994 | Chu | |
| 5,346,502 A | 9/1994 | Estabrook et al. | |
| 5,476,512 A | 12/1995 | Sarfarazi | |
| 5,476,514 A | 12/1995 | Cumming | |
| 5,476,515 A | 12/1995 | Kelman et al. | |
| 5,480,426 A | 1/1996 | Chu | |
| 5,484,447 A | 1/1996 | Waldock et al. | |
| 5,489,302 A | 2/1996 | Skottun | |
| 5,496,366 A | 3/1996 | Cumming | |
| 5,522,891 A | 6/1996 | Klaas | |
| 5,567,365 A | 10/1996 | Weinschenk et al. | |
| 5,571,177 A | 11/1996 | Deacon et al. | |
| 5,584,304 A | 12/1996 | Brady | |
| 5,607,472 A | 3/1997 | Thompson | |
| 5,628,795 A | 5/1997 | Langerman | |
| 5,674,282 A | 10/1997 | Cumming | |
| 5,684,637 A | 11/1997 | Floyd | |
| 5,722,952 A | 3/1998 | Schachar | |
| 5,752,960 A | 5/1998 | Nallakrishnan | |
| 5,766,244 A | 6/1998 | Binder | |
| 5,843,188 A | 12/1998 | McDonald | |
| 5,871,455 A | 2/1999 | Ueno | |
| 5,895,610 A | 4/1999 | Chang | |
| 5,919,230 A | 7/1999 | Sambursky | |
| 5,968,094 A | 10/1999 | Werblin et al. | |
| 5,984,962 A | 11/1999 | Anello | |
| 6,007,579 A | 12/1999 | Lipshitz et al. | |
| 6,027,531 A | 2/2000 | Tassignon | |
| 6,051,024 A | 4/2000 | Cumming | |
| 6,110,202 A | 8/2000 | Barraquer et al. | |
| 6,117,171 A | 9/2000 | Skottun | |
| 6,129,759 A | 10/2000 | Chambers | |
| 6,164,282 A | 12/2000 | Gwon et al. | |
| 6,193,750 B1 | 2/2001 | Cumming | |
| 6,197,057 B1 | 3/2001 | Peyman et al. | |
| 6,197,059 B1 | 3/2001 | Cumming | |
| 6,200,342 B1 | 3/2001 | Tassignon | |
| 6,280,469 B1 | 8/2001 | Terry et al. | |
| 6,280,471 B1 | 8/2001 | Peyman et al. | |
| 6,299,618 B1 | 10/2001 | Sugiura | |
| 6,299,641 B1 | 10/2001 | Woods | |
| 6,342,073 B1 | 1/2002 | Cumming et al. | |
| 6,387,126 B1 | 5/2002 | Cumming | |
| 6,406,494 B1 | 6/2002 | Laguette et al. | |
| 6,423,094 B1 | 7/2002 | Sarfarazi | |
| 6,443,984 B1 | 9/2002 | Jahn et al. | |
| 6,443,985 B1 | 9/2002 | Woods | |
| 6,464,725 B2 | 10/2002 | Skotton | |
| 6,488,708 B2 | 12/2002 | Sarfarazi | |
| 6,494,910 B1 | 12/2002 | Ganem et al. | |
| 6,494,911 B2 | 12/2002 | Cumming | |
| 6,503,276 B2 | 1/2003 | Lang et al. | |
| 6,506,212 B2 | 1/2003 | Zhou et al. | |
| 6,520,691 B2 | 2/2003 | Nomura et al. | |
| 6,524,340 B2 | 2/2003 | Israel | |
| 6,554,860 B2 | 4/2003 | Hoffmann et al. | |
| 6,570,718 B2 | 5/2003 | Nomura et al. | |
| 6,596,026 B1 | 7/2003 | Gross et al. | |
| 6,599,317 B1 | 7/2003 | Weinschenk, III et al. | |
| 6,605,093 B1 | 8/2003 | Blake | |
| 6,616,692 B1 | 9/2003 | Glick et al. | |
| 6,638,305 B2 | 10/2003 | Laguette | |
| 6,638,306 B2 | 10/2003 | Cumming | |
| 6,645,245 B1 | 11/2003 | Preussner | |
| 6,739,722 B2 | 5/2004 | Laguette et al. | |
| 6,749,634 B2 | 6/2004 | Hanna | |
| 6,790,232 B1 | 9/2004 | Lang | |
| 6,849,091 B1 | 2/2005 | Cumming | |
| 6,960,231 B2 | 11/2005 | Tran | |
| 6,972,033 B2 | 12/2005 | McNicholas | |
| 7,008,449 B2 | 3/2006 | Willis et al. | |
| 7,025,783 B2 | 4/2006 | Brady et al. | |
| 7,037,338 B2 | 5/2006 | Nagamoto | |
| 7,097,660 B2 | 8/2006 | Portney | |
| 7,118,597 B2 | 10/2006 | Miller et al. | |
| 7,122,053 B2 | 10/2006 | Esch | |
| 7,137,994 B2 | 11/2006 | De Juan, Jr. | |
| 7,220,279 B2 | 5/2007 | Nun | |
| 7,261,737 B2 | 8/2007 | Esch et al. | |
| 7,278,739 B2 | 10/2007 | Shadduck | |
| 7,350,916 B2 | 4/2008 | Hong et al. | |
| 7,815,678 B2 | 10/2010 | Ben Nun | |
| 7,842,087 B2 | 11/2010 | Ben Nun | |
| 7,854,764 B2 | 12/2010 | Ben Nun | |
| 7,976,520 B2 | 7/2011 | Ben Nun | |
| 7,998,199 B2 | 8/2011 | Ben Nun | |
| 8,048,156 B2 | 11/2011 | Geraghty et al. | |
| 2002/0103535 A1 | 8/2002 | Portney | |
| 2002/0103537 A1 | 8/2002 | Willis et al. | |
| 2003/0060881 A1 | 3/2003 | Glick et al. | |
| 2003/0097177 A1 | 5/2003 | Tran | |
| 2003/0109926 A1 | 6/2003 | Portney | |
| 2003/0149480 A1 | 8/2003 | Shadduck | |
| 2004/0073304 A1 | 4/2004 | Weinschenk, III et al. | |
| 2004/0148022 A1 | 7/2004 | Eggleston | |
| 2004/0169816 A1 | 9/2004 | Esch | |
| 2004/0181279 A1 | 9/2004 | Nun | |
| 2004/0220666 A1* | 11/2004 | Cumming | 623/6.18 |
| 2005/0090896 A1 | 4/2005 | Ben Nun | |
| 2005/0177229 A1 | 8/2005 | Boxer Wachler | |
| 2006/0069431 A1 | 3/2006 | Graney et al. | |
| 2006/0069433 A1 | 3/2006 | Nun | |
| 2006/0074487 A1 | 4/2006 | Gilg | |
| 2007/0027538 A1 | 2/2007 | Aharoni et al. | |
| 2007/0027541 A1* | 2/2007 | Aharoni et al. | 623/6.41 |
| 2007/0088433 A1 | 4/2007 | Esch et al. | |
| 2007/0093891 A1 | 4/2007 | Tabernero | |
| 2007/0123981 A1 | 5/2007 | Tassignon | |
| 2007/0129799 A1 | 6/2007 | Schedler | |
| 2007/0129801 A1 | 6/2007 | Cumming | |
| 2007/0129803 A1 | 6/2007 | Cumming | |
| 2007/0185574 A1 | 8/2007 | Ben Nun | |
| 2007/0244561 A1 | 10/2007 | Ben Nun | |
| 2008/0004699 A1 | 1/2008 | Ben Nun | |
| 2008/0188930 A1 | 8/2008 | Mentak et al. | |
| 2008/0300680 A1 | 12/2008 | Joshua | |

| | | | |
|---|---|---|---|
| 2009/0198247 A1 | 8/2009 | Ben Nun | |
| 2009/0264998 A1 | 10/2009 | Mentak et al. | |
| 2010/0121444 A1 | 5/2010 | Ben Nun | |

FOREIGN PATENT DOCUMENTS

| | | |
|---|---|---|
| EP | 0637503 B1 | 10/1998 |
| EP | 1 321 112 A | 6/2003 |
| FR | 2 794 965 | 12/2000 |
| JP | 2005007029 | 1/2005 |
| TW | 523408 | 3/2003 |
| WO | WO 95/20367 | 0/8199 |
| WO | WO 83/00998 | 3/1983 |
| WO | WO 94/28825 | 12/1994 |
| WO | WO 98/05273 | 2/1998 |
| WO | WO 98/10717 | 3/1998 |
| WO | WO 99/62434 | 12/1999 |
| WO | WO 00/30566 | 6/2000 |
| WO | WO 00/61036 | 10/2000 |
| WO | WO 00/66037 | 11/2000 |
| WO | WO 01/08606 | 2/2001 |
| WO | WO 01/60286 | 8/2001 |
| WO | WO 02/065951 | 8/2002 |
| WO | WO 03/000154 | 1/2003 |
| WO | WO 03/015669 | 2/2003 |
| WO | WO 2005/104994 | 11/2005 |
| WO | WO 2006/040759 | 4/2006 |
| WO | WO 2006/103674 | 5/2006 |
| WO | WO 2007/048615 | 5/2007 |
| WO | WO 2008/023379 | 2/2008 |
| WO | WO 2008/083283 A2 | 7/2008 |
| WO | WO 2008/097915 | 8/2008 |
| WO | WO 2008/107882 | 9/2008 |
| WO | WO 2009/122409 | 10/2009 |
| WO | WO 2010/010565 | 1/2010 |
| WO | WO 2012/023133 | 2/2012 |

OTHER PUBLICATIONS

Literature Review, Y. Ralph Cu et al, 2004 Accommodating IOLs by, Cataract & Refractive Surgery Today, May 2004, pp. 16, 17 & 20 (pp. 18 and 19 are not relevant to the literature review).

\* cited by examiner

UNITARY ACCOMMODATING INTRAOCULAR LENSES (AIOLS) AND DISCRETE BASE MEMBERS FOR USE THEREWITH

RELATED APPLICATIONS

The present application is a U.S. National Phase Application of International Application WO 2008/107882, filed on Mar. 5, 2008, which claims the benefit of Israel application no. 181710 filed on Mar. 5, 2007; Israel application no. 182604 filed on Apr. 17, 2007; and Israel application 185740 filed Sep. 5, 2007, all of which are herein incorporated by reference in their entirety.

FIELD OF THE INVENTION

The invention pertains to accommodating intraocular lens (AIOL) assemblies.

BACKGROUND OF THE INVENTION

Commonly owned PCT International Application No. PCT/IL02/00693 entitled Accommodating Lens Assembly and published on 27 Feb. 2003 under PCT International Publication No. WO 03/015669 illustrates and describes accommodating intraocular lens (AIOL) assemblies, the contents of which are incorporated herein by reference. The AIOL assemblies each include a haptics system adapted to be securely fixed in a human eye's annular ciliary sulcus at least two spaced apart stationary anchor points so that it may act as a reference plane for an AIOL of continuously variable Diopter strength affected by a human eye's capsular diaphragm under control of its sphincter-like ciliary body and acting thereagainst from a posterior direction. The haptics systems include a rigid planar haptics plate with a telescoping haptics member for sliding extension. The haptics plate and the haptics member are preferably self-anchoring as illustrated and described in commonly owned PCT International Application No. PCT/IL02/00128 entitled Intraocular Lens and published on 29 Aug. 2002 under PCT International Publication No. WO 02/065951, the contents of which are incorporated herein by reference.

Commonly owned PCT International Application No. PCT/IL2005/000456 entitled Accommodating Intraocular Lens Assemblies and Accommodation Measurement Implant and published on 10 Nov. 2005 under PCT International Publication No. WO 2005/104994 illustrates and describes AIOL assemblies enabling post implantation in situ manual selective displacement of an AIOL along a human eye's visual axis relative to at least two spaced apart stationary anchor points to a desired position to ensure that an AIOL assumes a non-compressed state in a human eye's constricted ciliary body state, the contents of which are incorporated herein by reference. Such in situ manual selective displacement can be effected post implantation to correct for capsular contraction which is a natural reaction which typically develops over a few months following extraction of the contents of a human eye's natural crystalline lens, and also a subject's changing eyesight overtime with minimal clinical intervention. Such in situ manual selective displacement can be achieved as follows: First, a discrete haptics system for retaining a discrete AIOL which is manually displaceable relative thereto. And second, a haptics system with at least two haptics having radiation sensitive regions capable of undergoing plastic deformation for in situ manual displacement of an integrally formed AIOL.

Commonly owned PCT International Application No. PCT/IL2005/001069 entitled Accommodating Intraocular Lens (AIOL), and Assemblies Including Same published on 20 Apr. 2006 under PCT International Publication No. WO 2006/040759 illustrates and describes an AIOL having a biasing mechanism for elastically deforming an elastically deformable shape memory disc-like optical element for affording a natural positive Diopter strength for near vision, the contents of which are incorporated herein by reference. The AIOL is intended to be implanted in a human eye such that relaxation of its ciliary body causes its capsular diaphragm to apply an accommodation force for overcoming the biasing mechanism to reduce the AIOL's natural positive Diopter strength for distance vision.

Commonly owned PCT International Application No. PCT/IL2006/000406 entitled Accommodating Intraocular Lens (AIOL) Assemblies, and Discrete Components Therefor published on 5 Oct. 2006 under PCT International Publication No. WO 2006/103674 illustrates and describes AIOL assemblies enabling post implantation in situ manual selective displacement of an AIOL along a human eye's visual axis relative to at least two spaced apart stationary anchor points to a desired position to ensure that an AIOL assumes a non-compressed state in a human eye's constricted ciliary body state, the contents of which are incorporated herein by reference. Additionally, WO 2006/103674 illustrates and describes preferred attachment plates for self-anchoring implantation in a human eye's annular ciliary sulcus.

Commonly owned PCT International Application No. PCT/IL2007/001056 entitled Intraocular Lens Implantation Kit published on 28 Feb. 2008 under PCT International Publication No. WO 2008/023379 illustrates and describes an IOL implantation kit for assisting in implanting an AIOL assembly in a human eye, the contents of which are incorporated herein by reference. The IOL implantation kit includes a forceps-like insertor tool for clamping an AIOL heightwise between its leading and trailing surfaces for assisting in anchoring its leading haptics in a distal segment of a human eye's ciliary sulcus. The implantation kit includes a crook-like insertor tool for assisting in fixating an AIOL assembly's trailing haptics in a human eye's ciliary sulcus generally diametrically opposite its leading haptics.

Deployment of AIOLs in a human eye involves capsulorhexis for preparing an aperture in the eye's anterior capsule for enabling removal of its natural crystalline lens content. Capsulorhexis typically involves preparing a circular aperture having a between about 4 to 5 mm diameter, thereby leaving an annular anterior capsule flange against which the aforesaid AIOLS are urged from an anterior direction. Such deployment may or may not lead to a human eye's annular anterior capsule flange overlie its still intact posterior capsule depending on the natural thickness of the human eye's natural crystalline lens content. Separation between a human eye's annular anterior capsule flange and its intact posterior capsule enables growth of epithelial cells which naturally migrate towards the center of the posterior capsule's anterior surface which induces a secondary cataract causing the posterior capsule to become opaque. Such secondary cataracts are necessarily removed by YAG laser to restore vision. Moreover, such separation also diminishes the forces available for acting upon the aforesaid AIOLs to mitigate their accommodative capability compared to their theoretical accommodative power.

SUMMARY OF THE INVENTION

The present invention is directed towards unitary accommodating intraocular lenses (AIOLs) including a haptics system with a pair of diametrically opposite elongated generally C-shaped haptics for self-anchoring in a human eye's ciliary sulcus integrally formed with a general disc-like resiliently elastically compressible shape memory optical element having a continuously variable Diopter strength between a first preferably zero Diopter strength in a non-compressed state and a second Diopter strength different than its first Diopter strength in a compressed state. The unitary AIOLs include an optical element with an exposed trailing surface and are intended to be used in conjunction with a discrete base member for applying an axial compression force from a posterior direction for compressing their optical elements from a non-compressed state to a compressed state on relaxation of a human eye's ciliary body from a contracted ciliary body state to a relaxed ciliary body state whereupon an optical element reverts to its non-compressed state on contraction of the human eye's ciliary body. The unitary AIOLS are preferably designed to be used with either a purpose designed base member implanted immediately prior to an AIOL typically during the same surgical procedure or a previously implanted standard in-the-bag IOL acting as a base member. Alternatively, the unitary AIOLs can be designed to be solely used with purpose designed base members.

The unitary AIOLs include a haptics main body designed to undergo elastic deformation on being squeezed by a pincer-like compression force to an elliptic shape to reduce their width for lengthwise insertion into a small corneal incision in the range of about 3 mm to about 4 mm to assist implantation. The unitary AIOLs preferably include a tubular haptics ring and a tubular interposer deployed between a haptics ring and an optical element. Interposers include a leading inwardly directed annular flange defining an aperture through which an optical element anteriorly bulges therethrough on application of an axial compression force from a posterior direction. Interposers are formed from pliable material such that their leading inwardly directed annular flanges give on application of an axial compression force to avoid a sharp transition of an anteriorly bulging optical element at an annular flange's rim to reduce optical aberrations. Interposers also preferably include a trailing outwardly directed annular flange for abutting against a haptics ring's trailing end face to ensure their secure deployment in the unitary AIOLs.

The unitary AIOLs preferably include a so-called Vertical Adjustment Mechanism (VAM) for enabling in situ longitudinal displacement of their optical elements relative to their stationary anchoring points. The VAMs are implemented by each haptics having a heat deformable region adjacent its haptics main body. The heat deformable regions are intended to undergo localized heating by an external energy source for enabling plastic deformation of the haptics at a so-called glass transition temperature. Localized heating can be achieved by inter alia irradiation by a laser source, induced heating by a RF source, a heat probe, and the like, to a temperature higher than a human eye's normal 36° C. temperature but sufficiently low so as not to damage a human eye's delicate internal structures.

The optical elements preferably include a peripheral surface designed to minimize resistance to an axial compression force for anteriorly bulging same. Such resistance can be reduced by the provision of a peripheral surface with a bellows-like trailing section, a beveled trailing edge, and the like. The optical elements may include a trailing bulge control element for further facilitating anterior bulging during compression to a desired curved shape to improve acuity of vision. The bulge control elements may be in the form of an embedded rounded core or a rounded recess for snug insertion of a complementary rounded projection on a purpose built base member.

Purpose designed base members for use in conjunction with the unitary AIOLs preferably have an elongated substantially planar main body with opposite leading and trailing ends. The base members have a central piston member and lateral wings with a tapering thickness such that they are readily flexible to conform to the natural curvature of a human eye's capsular diaphragm on implantation. The base members have a leading end which is initially manipulated into a desired location in a human eye's ciliary sulcus during implantation and a trailing end which is subsequently manipulated at a general diametrically opposite location to the leading end by the aforesaid commonly owned WO 2008/023379's crook-like insertor tool. The trailing ends are preferably formed with throughgoing manipulation bores for facilitating in situ manipulation.

The piston members have a leading working surface for acting against a unitary AIOL's optical element's trailing surface and a trailing working surface for being urged in an anterior direction by a human eye's capsular diaphragm. The leading working surfaces are preferably formed with an alignment element for axially aligning a unitary AIOL with a base member on implantation in a human eye. The alignment elements can be in the form of either a circular depression for use with unitary AIOLs having a protruding optical element or a leading disc-like step for use with unitary AIOLs having a flush or a recessed optical element. Additionally, the leading working surfaces can be formed with a rounded bulge control core for both alignment purposes and also assisting in the controlled anterior bulging of an AIOL having an optical element with a posterior surface having a complementary rounded recess.

The posterior surfaces can be fashioned to meet different clinical conditions and/or optionally provide additional positive dioptric power if so required. For example, trailing working surfaces can be formed with a trailing disc-like step for protruding through a human eye's post capsulorhexis anterior capsule for ensuring that a base member simultaneously contacts a human eye's anterior capsule and its posterior capsule which are not directly overlying. The posterior surfaces in general and the trailing working surfaces in particular can be flat with no dioptric value or convex with positive dioptric value. Moreover, the trailing disc-like steps act as a mechanical barrier for stopping the natural migration of epithelial cells towards a human eye's visual axis thereby precluding the natural formation of secondary cataracts in the case of a human eye's annular anterior capsule flange not overlying its intact posterior capsule subsequent to capsulorhexis and subsequent to lens content removal.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF PREFERRED EMBODIMENTS OF THE PRESENT INVENTION

Figure 1:
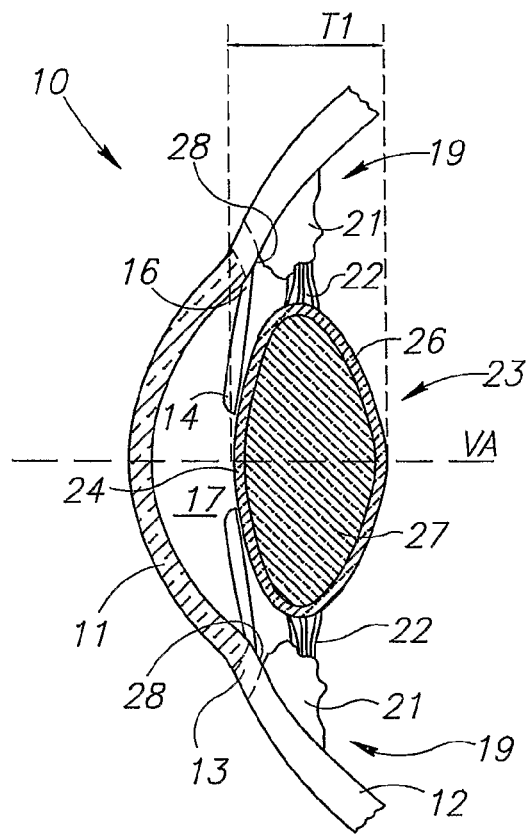
FIG. 1 is a cross section view of an anterior part of a human eye in its contracted ciliary body state for natural near vision in an axial plane of the human body.
Figure 2:
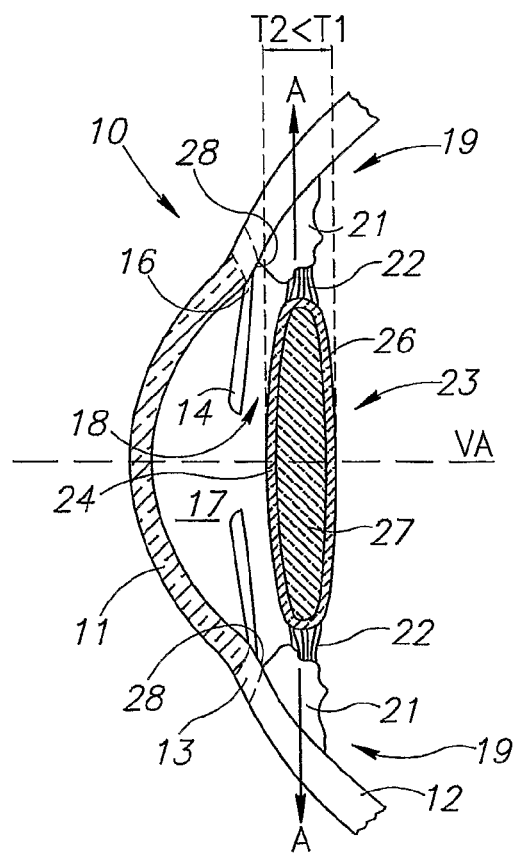
FIG. 2 is a cross section view of an anterior part of a human eye in its relaxed ciliary body state for natural distance vision in an axial plane of the human body.

FIGS. 1 and 2 are cross section views of an anterior part of a human eye 10 having a visual axis VA in its natural near and distance vision conditions, respectively, in an axial plane of the human body. The human eye 10 has a cornea 11 peripherally connected to a spherical exterior body made of tough connective tissue known as the sclera 12 at an annular sclero-corneal juncture 13. An iris 14 inwardly extends into the human eye 10 from its root 16 at the sclero-corneal juncture 13 to divide the human eye's anterior part into an anterior chamber 17 and a posterior chamber 18. A sphincter-like peripheral structure known as the ciliary body 19 includes ciliary processes housing ciliary muscles 21 fired by parasympathetic nerves. The ciliary muscles 21 are connected to zonular fibers 22 which in turn are peripherally connected to the equatorial edge of a membrane known as the capsular bag 23 with an anterior capsule 24 and a posterior capsule 26 enrobing a natural crystalline lens 27. The iris's root 16 and the ciliary body 19 delimit a portion of the interior surface of the sclera 12 at the sclero-corneal juncture 13 known as the ciliary sulcus 28. Remnants of the anterior capsule 24 which may remain after extraction of the natural crystalline lens 27 and the intact posterior capsule 26 are referred to hereinafter as the capsular diaphragm 29. Contraction of the ciliary body 19 allows the lens 27 to thicken to its natural thickness T1 along the visual axis VA for greater positive optical power for near vision (see FIG. 1). Relaxation of the ciliary body 19 tensions the zonular fibers 22 which draws the capsular bag 23 radially outward as shown by arrows A for compressing the lens 27 to shorten its thickness along the visual axis VA to T2<T1 for lower positive optical power for distance vision (see FIG. 2).

Unitary Accommodating Intraocular Lenses (AIOLs)

Figure 5:
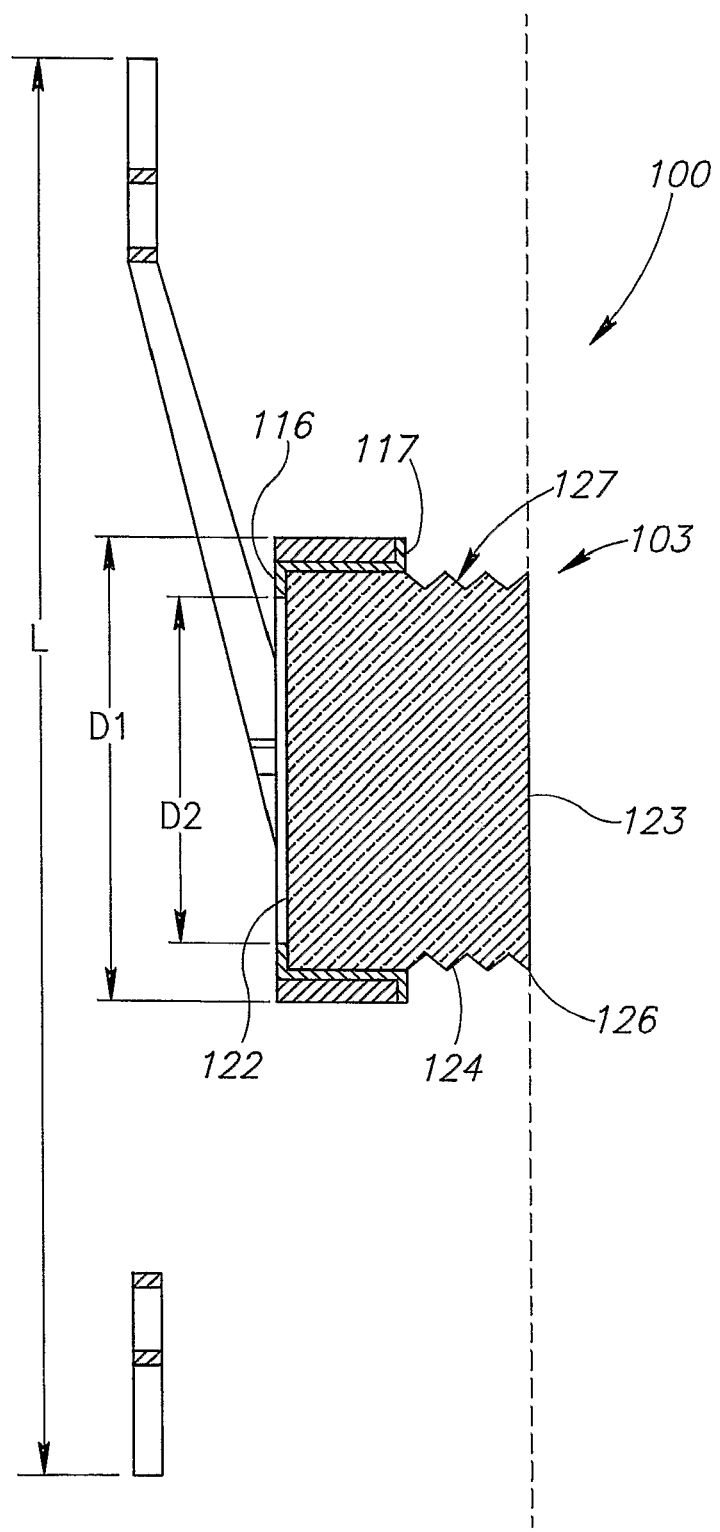
FIG. 5 is a longitudinal cross section of FIG. 3's unitary AIOL in a non-compressed state along line A-A in FIG. 3.
Figure 6:
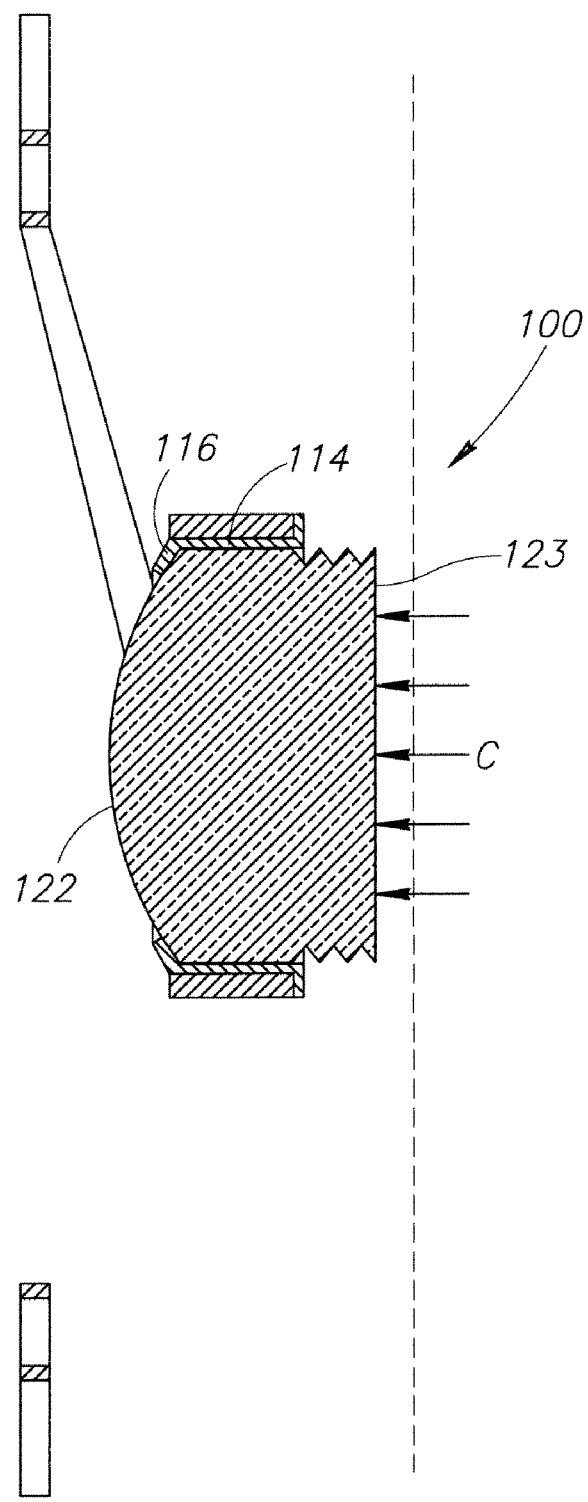
FIG. 6 is a longitudinal cross section of FIG. 3's unitary AIOL in a compressed state along line A-A in FIG. 3.
Figure 7:
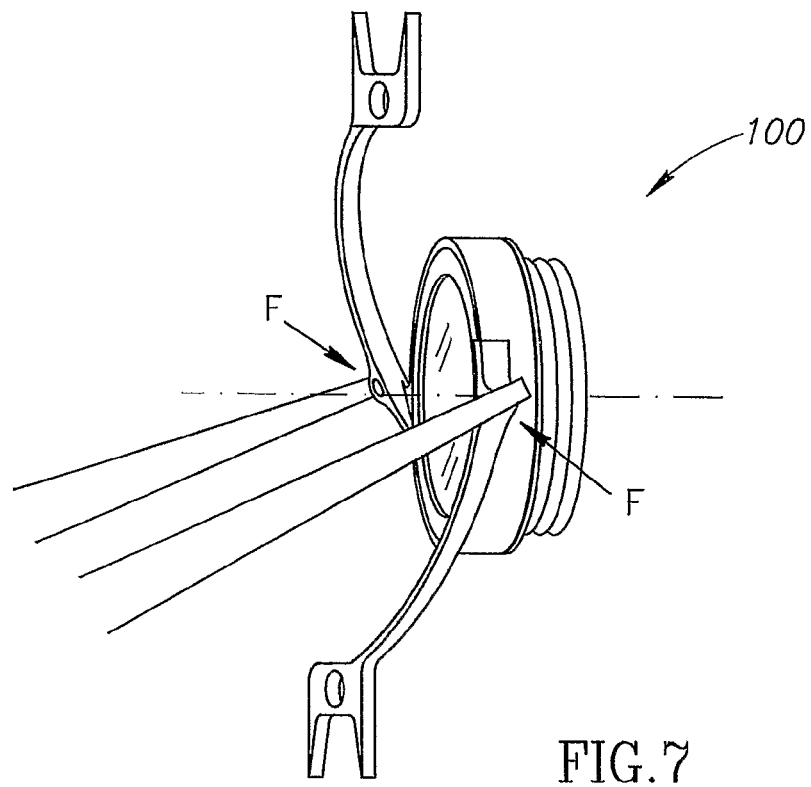
FIG. 7 is a perspective view of FIG. 3's unitary AIOL on application of a pincer-like compression force on its haptics main body for squeezing same into an elliptic shape for reducing its width for insertion of the unitary AIOL through a corneal incision for implantation purposes.

FIGS. 3 to 20 show unitary AIOLs 100 for use in conjunction with a discrete base member implemented as either a purpose designed base member or a previously implanted in the bag IOL. The unitary AIOLs 100 have a longitudinal axis 101 intended to be co-directional with a human eye's visual axis VA on implantation in a human eye 10. The unitary AIOLs 100 include a haptics system 102 for self-anchoring in a human eye's ciliary sulcus 28 and house a resiliently elastically compressible disc-like shape memory optical element 103. The haptics systems 102 are made from suitable rigid bio-compatible transparent polymer material such as PMMA, and the like. The optical elements 103 are made from suitable bio-compatible transparent material such as silicon based gels and the like having a hardness typically rated in the region of 30±10 on the Shore Range 00. The optical elements 103 have a continuously variable Diopter strength between a first preferably zero Diopter strength in a non-compressed state (see FIG. 5) and a second Diopter strength different than its first Diopter strength in a compressed state on application of an axial compression force as indicated by arrows C in FIG. 6. The unitary AIOLs 100 are pre-assembled using conventional assembly techniques, for example, gluing, soldering, and the like.

The haptics systems 102 have a haptics length L and include a haptics main body 104 with a leading inwardly directed annular flange 106 defining a preferably circular aperture 107 through which the optical element 103 bulges therethrough on application of an axial compression force from a posterior direction, and an opposite trailing end face 108. The haptics main bodies 104 have an optics diameter D1 and the apertures 107 have a diameter D2 determining the active optical element surface of an optical element 103 in terms of its anterior bulging on application of an axial compression force. The haptics main bodies 104 are designed to be squeezable on application of a pincer-like compression force such that they temporarily and reversibly assume an elliptic shape to reduce their width for lengthwise insertion into a small corneal incision to assist implantation (see FIG. 7).

Unitary AIOLs 100 have exemplary dimensions as follows:

| | |
|---|---|
| Haptics Length L: | 13-15 mm |
| Optical Element Diameter D1: | 5-7 mm |
| Active Optical Element Surface Diameter D2: | 3.5-6 mm |

The haptics main bodies 104 include a pair of diametrically opposite elongated generally C-shaped haptics 109 extending in opposite directions in a plane perpendicular to the longitudinal axis 101. The haptics main bodies 104 include a tubular single continuous haptics ring 111 having opposite leading and trailing end faces 112 and 113 and an annular interposer 114 disposed between the haptics ring 111 and the optical element 103. The interposers 114 have a leading inwardly directed annular flange 116 constituting the annular flange 106 and a trailing outwardly directed annular flange 117 for abutting against a haptics rings trailing end face 113 to ensure their secure deployment in the unitary AIOLs 100. In this case, the annular flanges 117 constitute a haptics main body's trailing end face 108. The interposers 114 are preferably formed from pliable material such that their annular flanges 116 give on application of an axial compression force C to prevent formation of a sharp angle on bulging through the aperture 107 (see FIG. 6).

Figure 3:
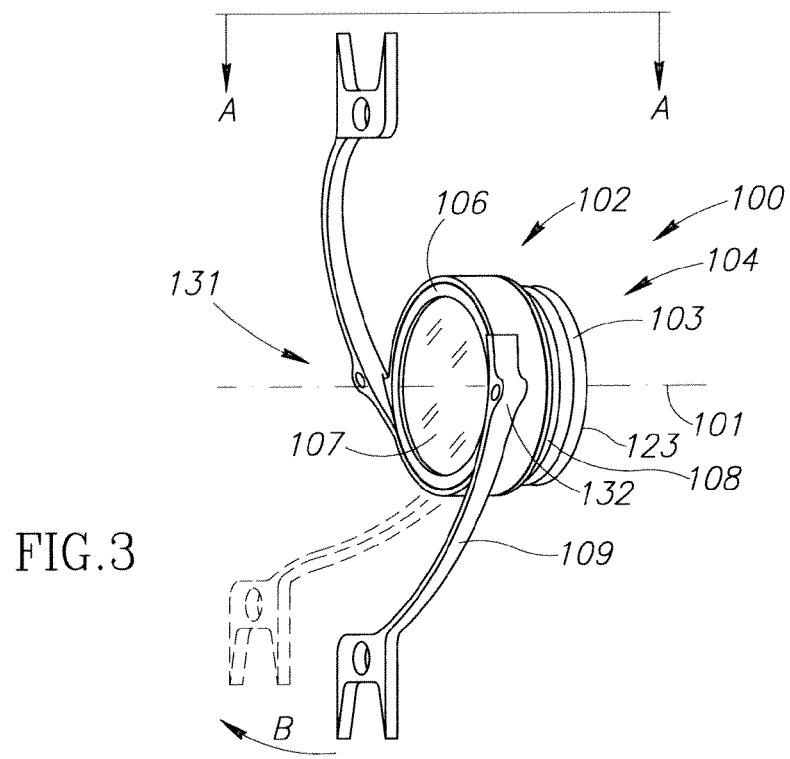
FIG. 3 is a perspective view of a unitary AIOL including a haptics system having a haptics main body with a trailing end face and a Vertical Adjustment Mechanism (VAM), a tubular interposer, and a compressible disc-like shape memory optical element with an exposed trailing surface protruding with respect to the haptics main body's trailing end face.

The haptics 109 have a thin profile in the plane perpendicular to the longitudinal axis 101 such that they are sufficiently flexible under reasonable forces as can be applied using conventional ophthalmic surgical tools for encircling around the haptics main body 104 shown by arrow B for facilitating insertion of the unitary AIOLs 100 into a human eye through a relatively small incision. FIG. 3 shows a haptics 109 in dashed lines for showing its encircling around the haptics main body 104. The haptics 109 have a wide profile along the longitudinal axis 101 such that they are rigid against a compression force therealong. The haptics' wide profile preferably tapers from its proximal end 109A adjacent the haptics main body 104 to its distal end 109B remote therefrom and terminating at a bifurcated attachment plate 118. The attachment plates 118 include a pair of spaced apart puncturing members 119 having tips 121 with a minimum tip separation of at least 1 mm and preferably between about 2 mm and 3 mm and a minimum tip height of at least 0.5 mm such that they can penetrate slightly more than half of a sclera's thickness of about 1 mm thereby providing a unitary AIOL 100's anchoring points.

Figure 21:
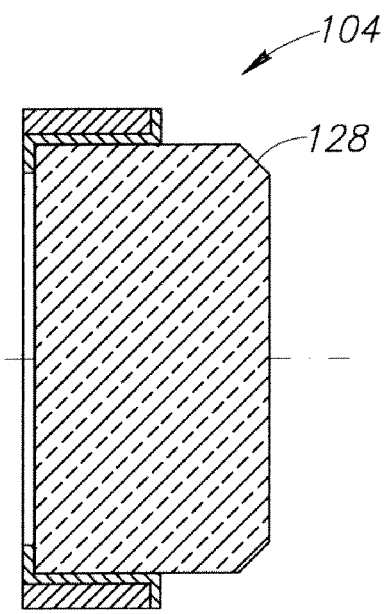
FIG. 21 is a longitudinal cross section of a haptics main body with an optical element with a chamfered trailing edge.
Figure 22:
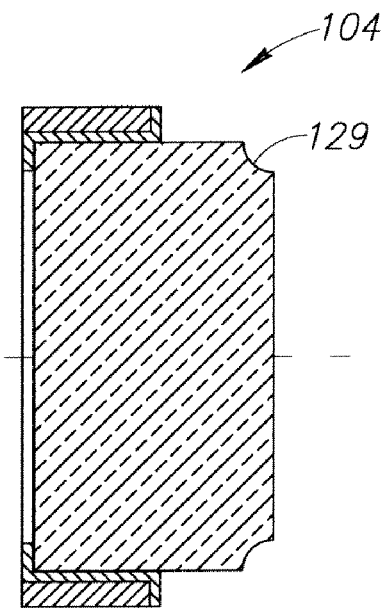
FIG. 22 is a longitudinal cross section of a haptics main body with an optical element with a fillet shaped trailing edge.
Figure 23:
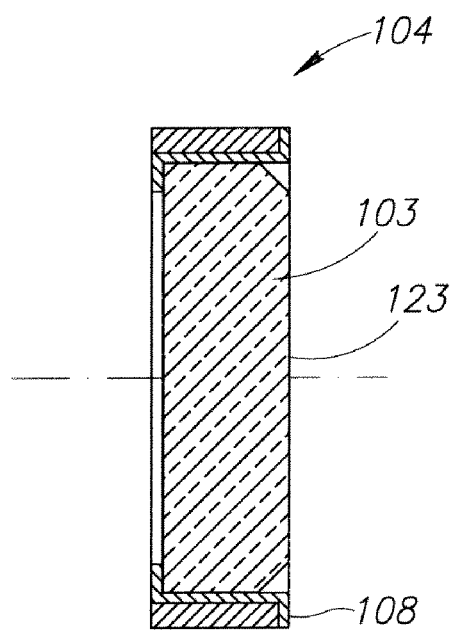
FIG. 23 is a longitudinal cross section of a haptics main body with a trailing end face and an optical element with a trailing surface flush therewith.
Figure 24:
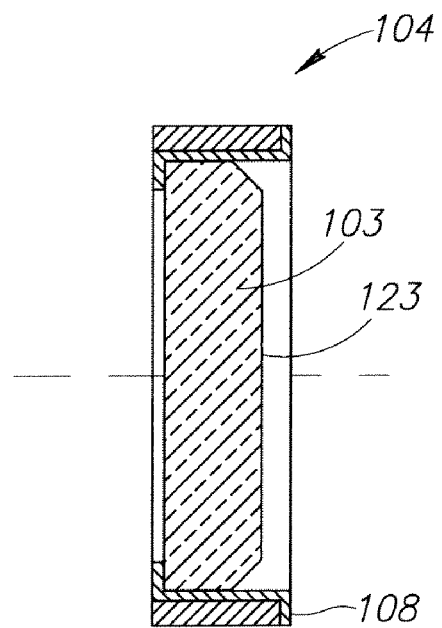
FIG. 24 is a longitudinal cross section of a haptics main body with a trailing end face and an optical element with a trailing surface recessed with respect thereto.

The optical elements 103 have a leading surface 122 and an opposite exposed trailing surface 123, and a peripheral surface 124 with a trailing edge 126. The optical elements 103 are preferably dimensioned such that their exposed trailing surfaces 123 protrude with respect to a haptics main body's trailing end face 108. The peripheral surfaces 124 are designed to facilitate compression of an optical element 103 by an axial compression force. This can be achieved by a peripheral surface 124 being formed with a bellows-like trailing section 127 extending beyond a haptics main body's trailing end face 108. Alternatively, trailing edges 126 can be beveled to reduce the resistance to an axial compression force. Beveling can be in the form a chamfered trailing edge 128 (see FIG. 21), a fillet shaped edge 129 (see FIG. 22), and the like. Alternatively, the optical elements 103 can be dimensioned such that their exposed trailing surfaces 123 are respectively flush with and recessed with respect to a haptics main body's trailing end face 108 (see FIGS. 23 and 24).

The haptics systems 102 preferably include a Vertical Adjustment Mechanism (VAM) 131 for enabling in situ longitudinal displacement of a haptics main body 104 relative to a unitary AIOL 100's anchoring points along a visual axis VA thereby controlling the position of the haptics main body 104 relative to an eye's capsular diaphragm 29. The VAMs 131 enable in situ correction of the placement of a unitary AIOL 100 in case it is placed too posterior or alternatively in case of excessive pressure being developed by an eye's capsular diaphragm. The VAMs 131 include the provision of each haptics 109 with a heat deformable region 132 adjacent a haptics main body 104 and intended to undergo local heating by an external energy source.

Figure 4:
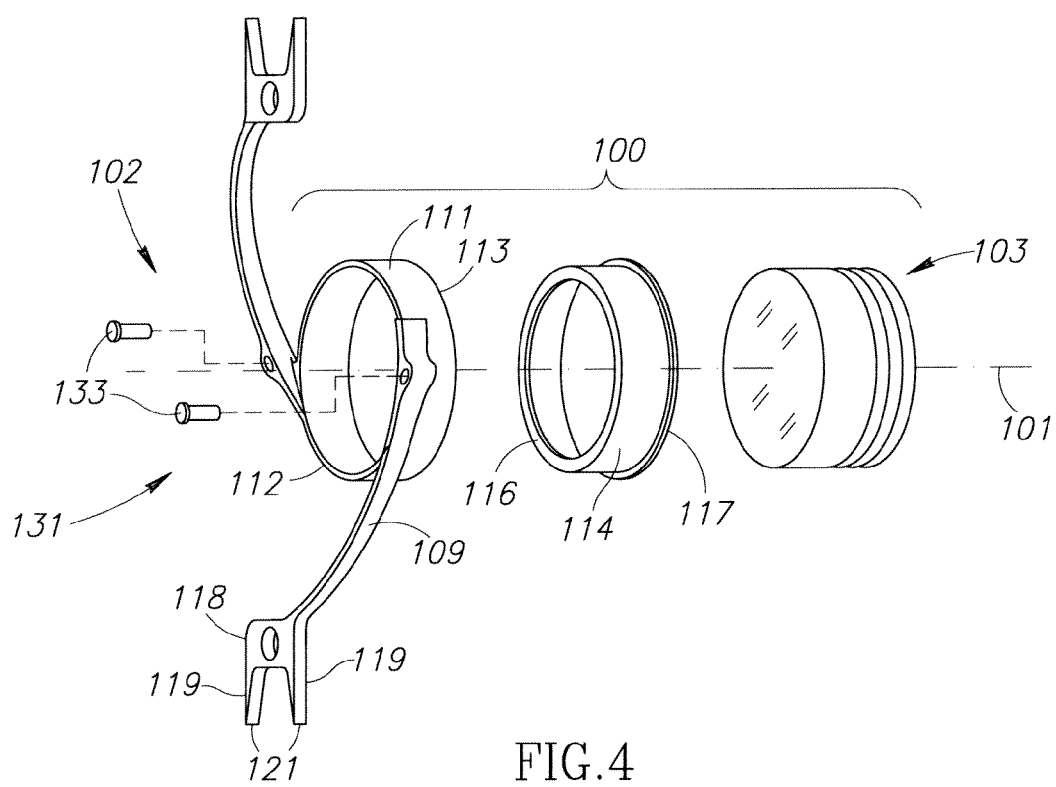
FIG. 4 is an exploded view of FIG. 3's unitary AIOL.
Figure 8:
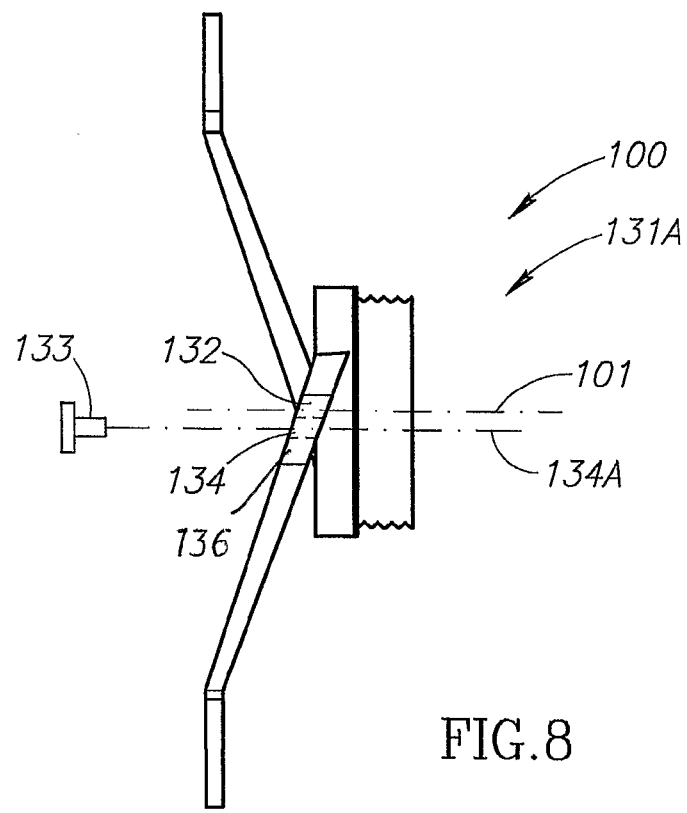
FIG. 8 is a side view of FIG. 3's unitary AIOL.
Figure 9A:
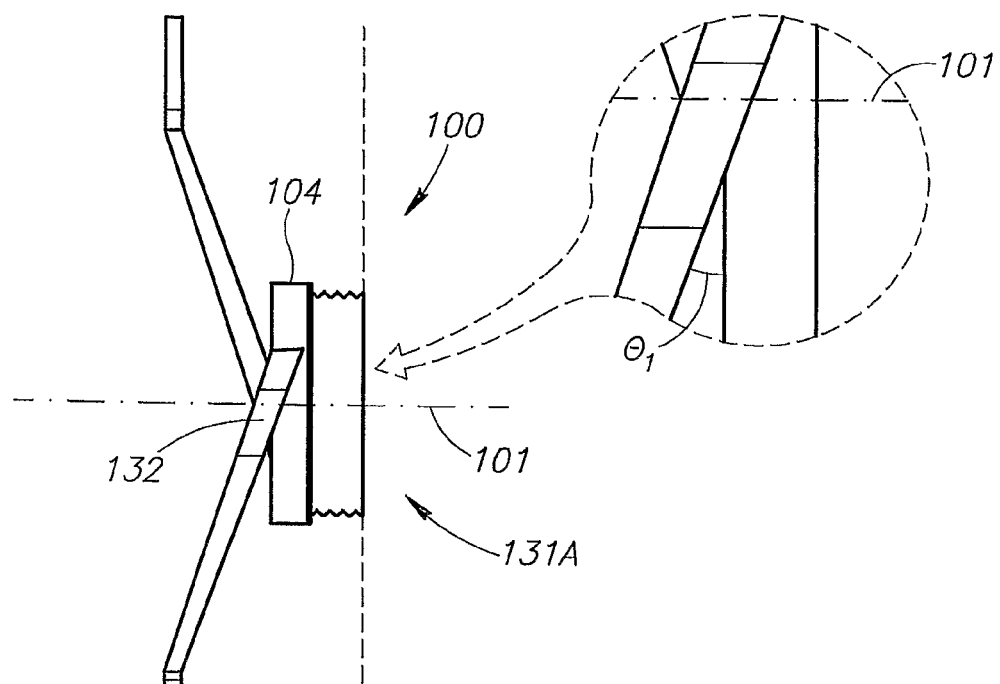
FIGS. 9A and 9B are side views of FIG. 3's unitary AIOL in a first axial position and a second axial position in front of the first axial position, respectively.
Figure 9B:
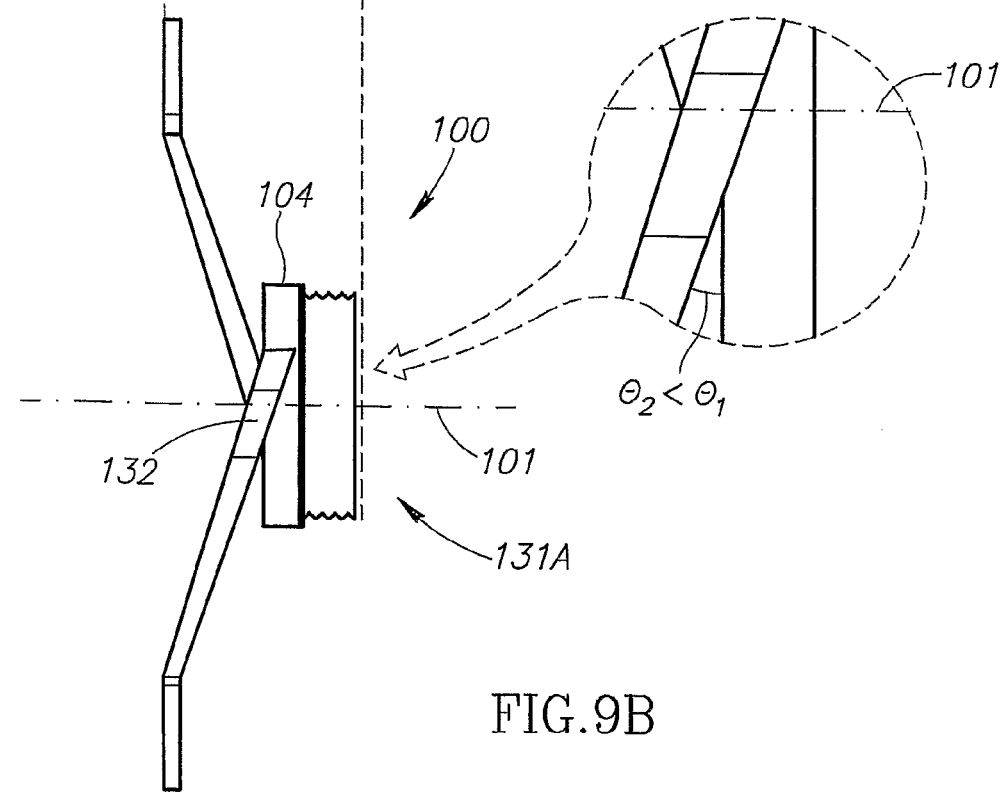

FIGS. 4 and 8 show a VAM 131A including tack-like radiation sensitive members 133 for insertion into blind bores 134 in outwardly rounded holders 136 adjacent a haptics main body 104 and having a longitudinal axis 134A co-directional with the longitudinal axis 101. The radiation sensitive members 133 are preferably formed from a low specific heat metal, for example, titanium, and the like, and are preferably pigment coated. The radiation sensitive members 133 are intended to be irradiated with suitable laser light, for example, for retinal photocoagulation, laser trabeculopasty, and the like, for enabling localized heating of their respective heat deformable regions 132 to a temperature higher than a human eye's normal 36° C. temperature but sufficiently low so as not to damage a human eye's delicate internal structures. Suitable laser systems include inter alia the Oculight SL 810 nm Infrared Photocoagulator commercially available from IRIDEX Corporation, California, USA www.iridex.com. FIGS. 9A and 9B show the unitary AIOL 100 in two different axial positions along the longitudinal axis 101 as determined by the angles θ1 and θ2 where θ2<θ1 such that unitary AIOL 100's position in FIG. 9B is more anterior than in FIG. 9A.

Figure 10A:
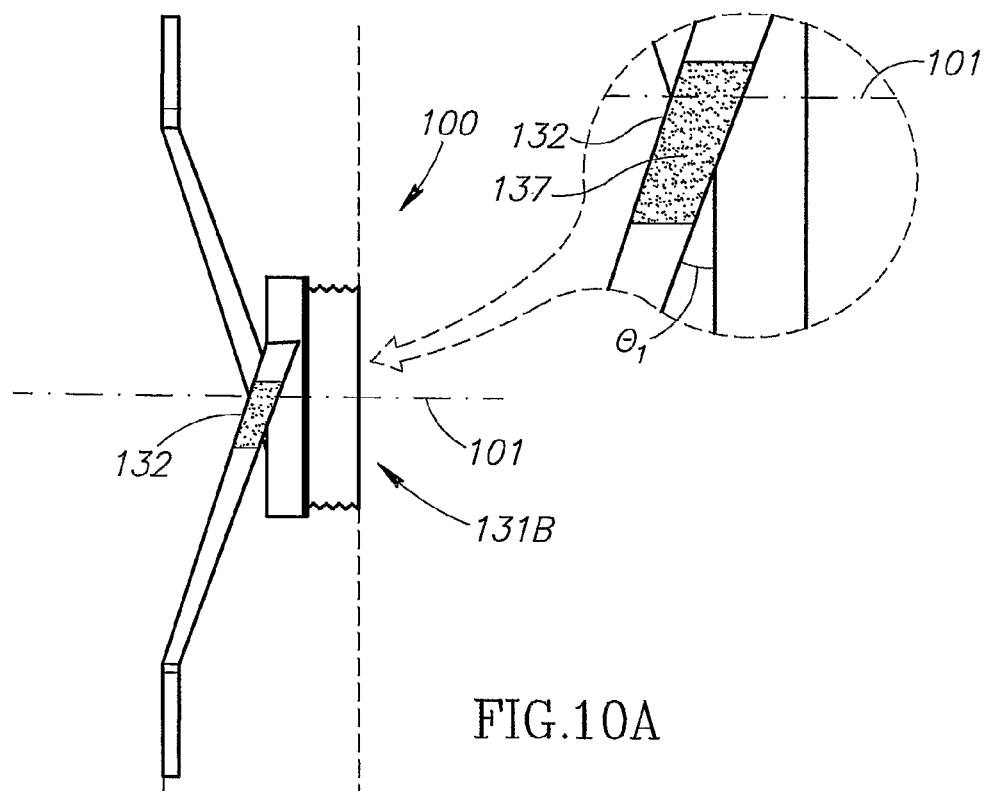
FIGS. 10A and 10B are side views of a unitary AIOL with an alternative VAM in a first axial position and a second axial position in front of the first axial position, respectively.
Figure 10B:
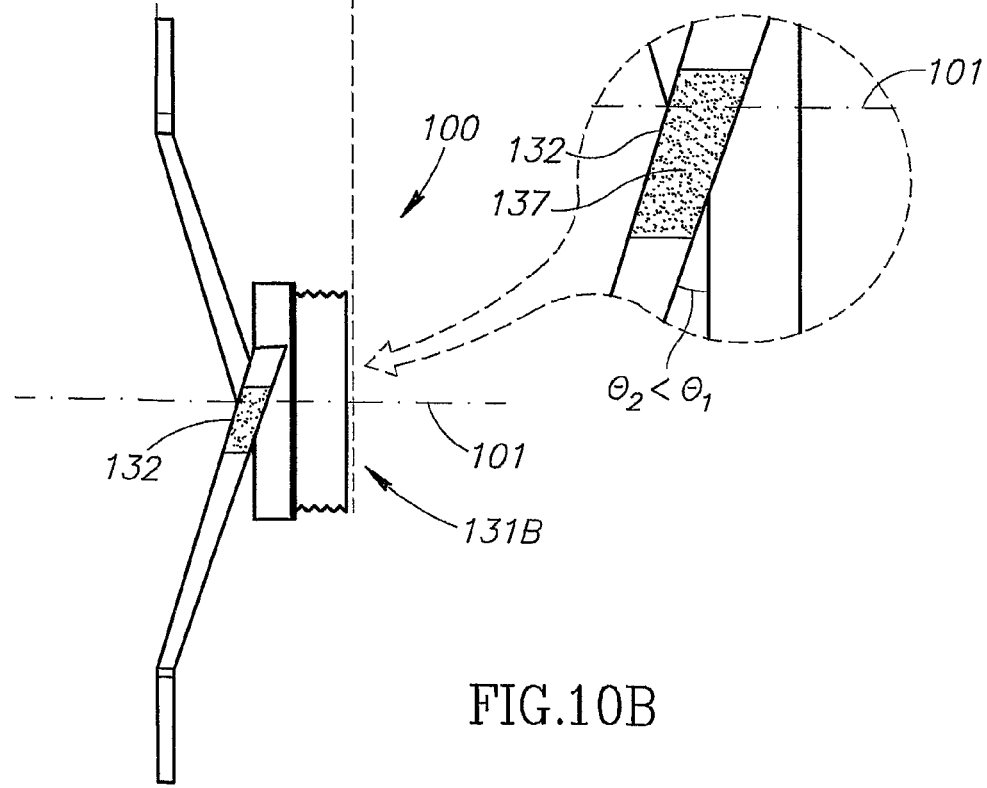

FIGS. 10A and 10B show a unitary AIOL 100 with a VAM 131B including heat deformable regions 132 impregnated with radiation sensitive bio-compatible chemicals 137, for example, Infra Red (IR) sensitive indocyanine green (ICG), and the like.

Figure 11:
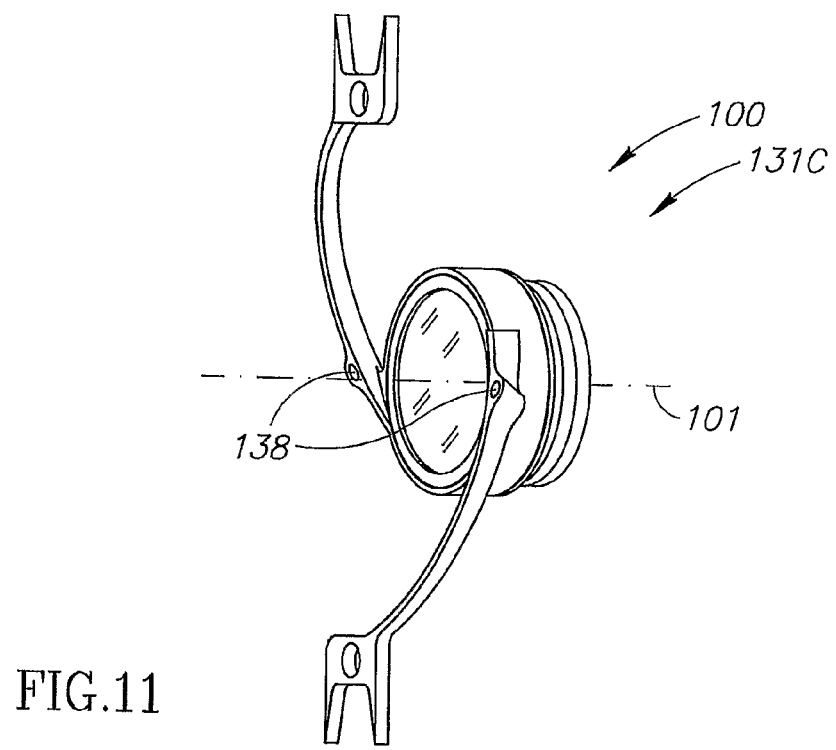
FIG. 11 is a perspective view of a unitary AIOL with another alternative VAM.
Figure 12:
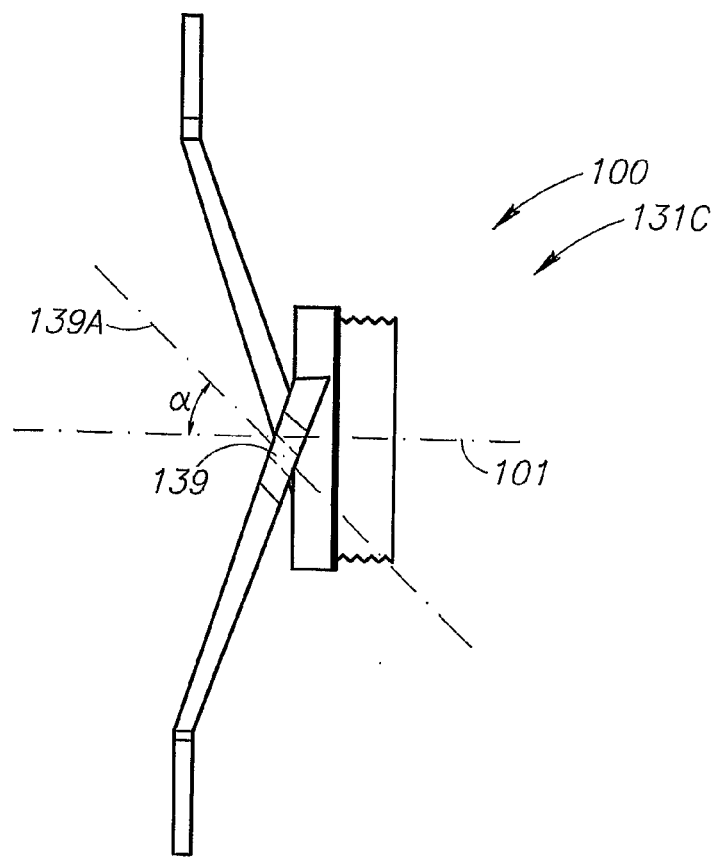
FIG. 12 is a side view of FIG. 11's unitary AIOL.
Figure 13:
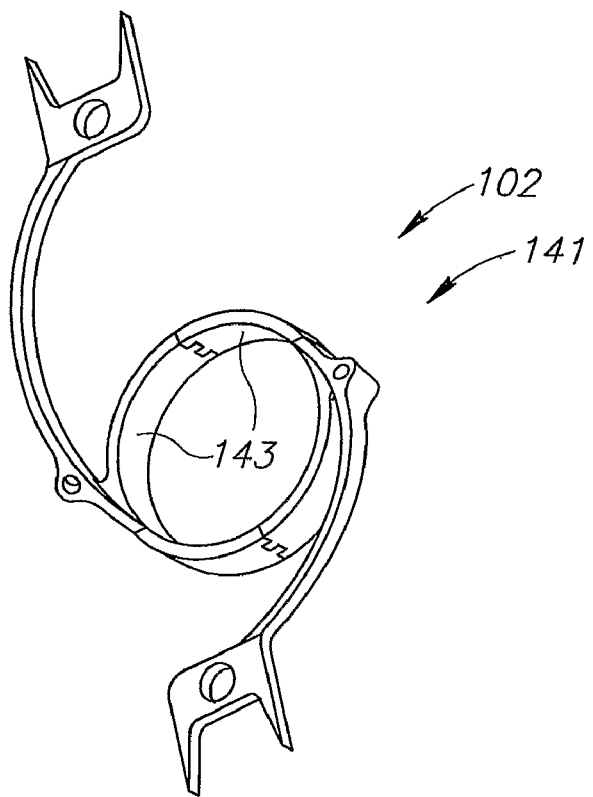
FIG. 13 is a perspective view of a haptics ring with a split ring arrangement including a pair of interlocking ring elements.
Figure 14:
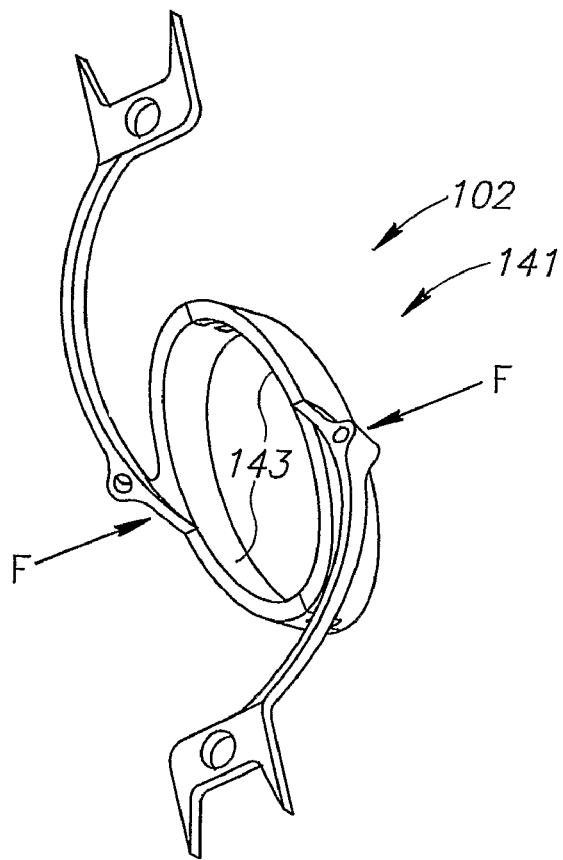
FIG. 14 is a perspective view of FIG. 13's haptics ring on application of a pincer-like compression force for squeezing it into an elliptic shape.
Figure 15:
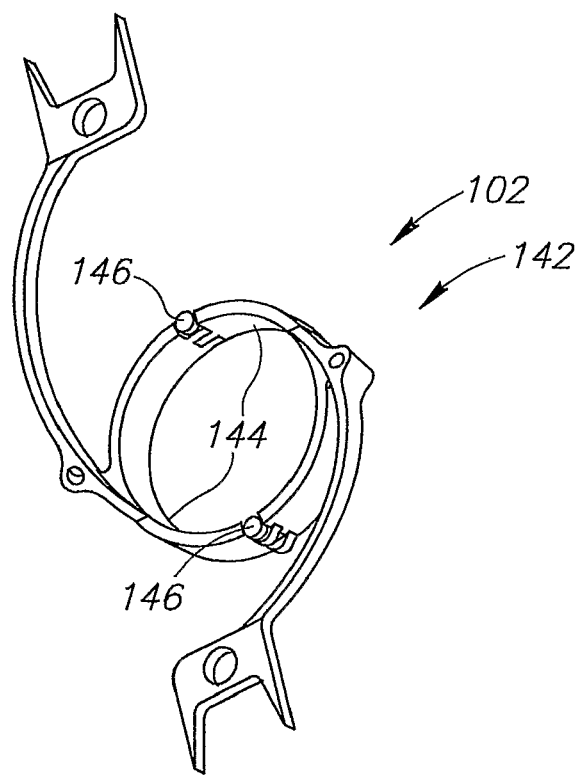
FIG. 15 is a perspective view of a haptics ring with a split ring arrangement including a pair of hinged ring elements.
Figure 16:
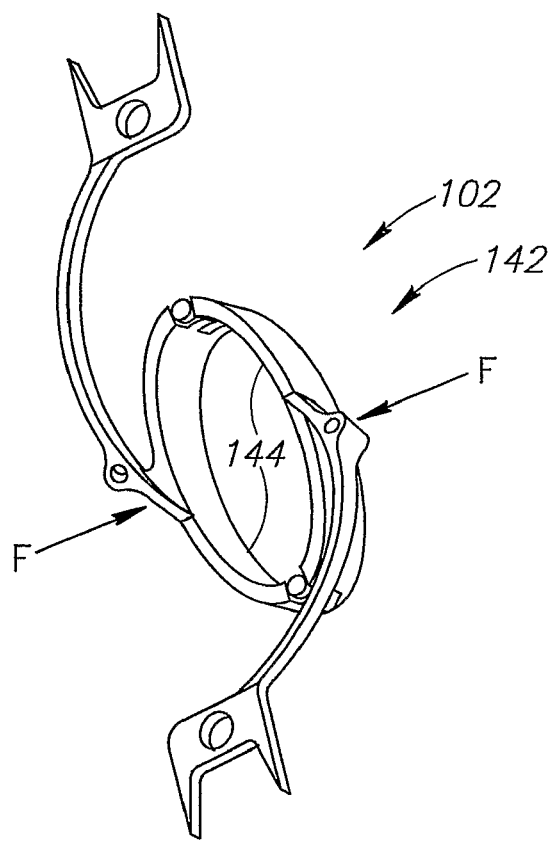
FIG. 16 is a perspective view of FIG. 15's haptics ring on application of a pincer-like compression force for squeezing it into an elliptic shape.

FIGS. 11 and 12 show a unitary AIOL 100 with a VAM 131C including metal elements 138 inserted in bores 139 having a longitudinal axis 139A inclined with respect to the longitudinal axis 101 at an included angle α≈45° wherein the metal elements 138 are intended to be heated by an external heat probe.

FIGS. 13 to 16 show the haptics systems 102 can include haptics rings 141 and 142 with split ring arrangements instead of a single continuous tubular haptics ring 111 for facilitating their squeezing into an elliptic shape on application of a pincer-like compression force thereby reducing their width for insertion through smaller corneal incisions. The haptics ring 141 includes a pair of interlocking ring elements 143 and the haptics ring 142 includes a pair of hinged ring elements 144 and a pair of hinge pins 146. The haptics rings 141 and 142 can each include two or more pairs of ring elements. The haptics rings 141 and 142 preferably undergo overmolding to ensure their structural integrity and a smooth outer finish.

Figure 17:
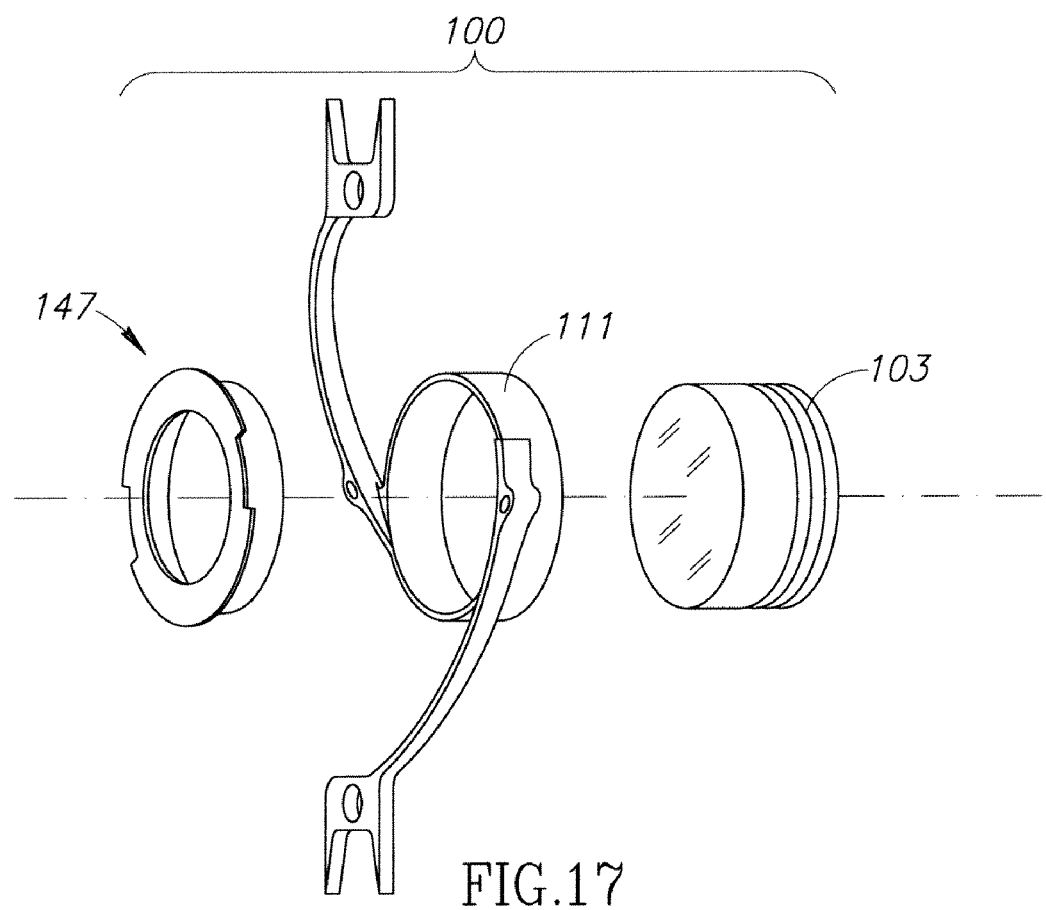
FIG. 17 is an exploded view of a unitary AIOL including a haptics main body having a tubular interposer with a modified cross section with respect to FIG. 3's tubular interposer.
Figure 18:
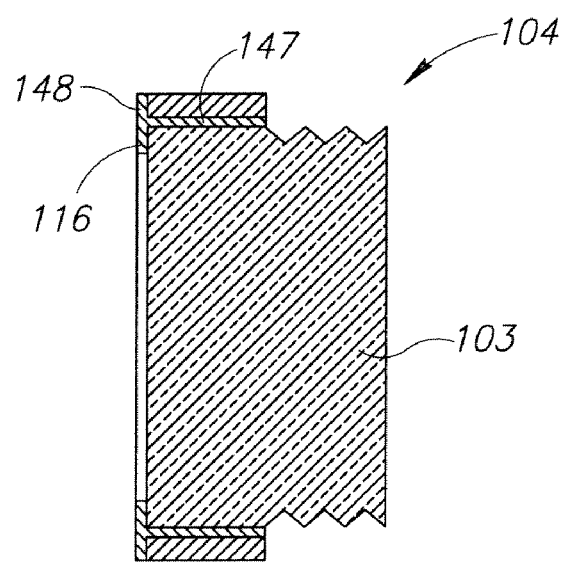
FIG. 18 is a longitudinal cross section of FIG. 17's haptics main body.

FIGS. 17 and 18 show a unitary AIOL 100 with a haptics main body 104 including the haptics ring 111 and an annular interposer 147 including the leading inwardly directed annular flange 116 and a leading outwardly directed annular flange 148. The interposer 147 can be conveniently mounted onto the haptics ring 111 from an anterior direction.

Figure 19:
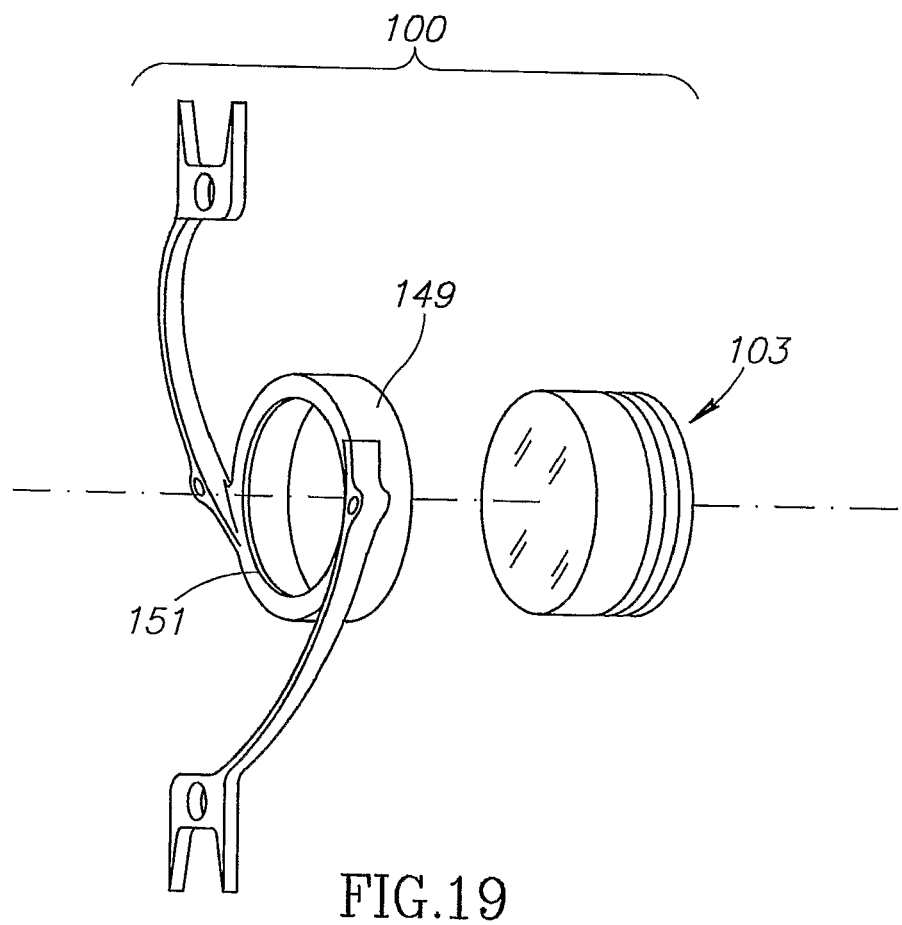
FIG. 19 is an exploded view of a unitary AIOL including a haptics main body having a haptics ring with an integrally formed leading inwardly directed annular flange.
Figure 20:
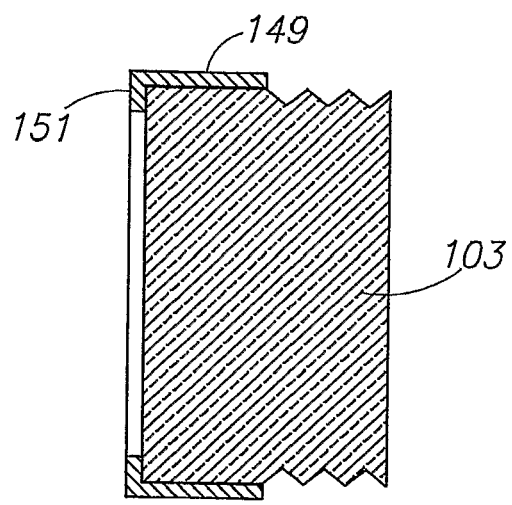
FIG. 20 is a longitudinal cross section of FIG. 19's haptics main body.

FIGS. 19 and 20 show a unitary AIOL 100 with a haptics main body 104 including a haptics ring 149 integrally formed with a leading inwardly directed annular flange 151 constituting the leading inwardly directed flange 116.

Figure 25:
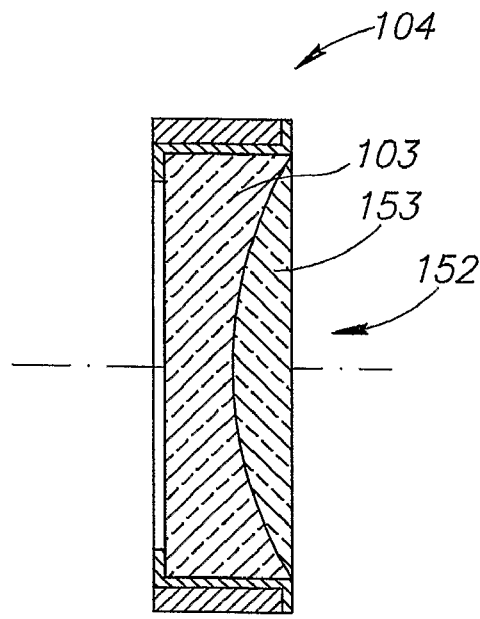
FIG. 25 is a longitudinal cross section of a haptics main body including an optical element with a rounded bulge control element in the form of an embedded spherical core for controlling anterior bulging.
Figure 26:
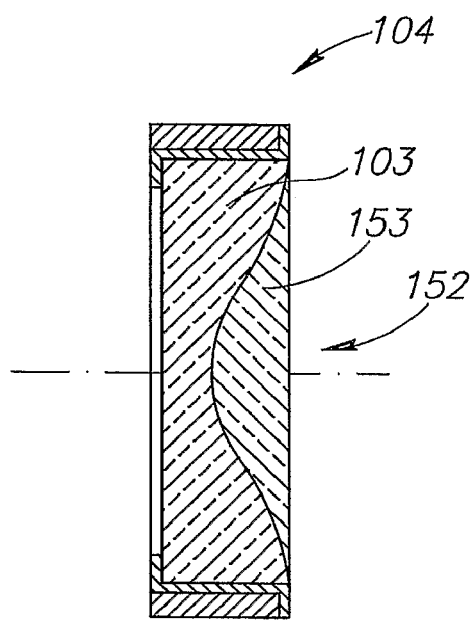
FIG. 26 is a longitudinal cross section of a haptics main body including an optical element with a rounded bulge control element in the form of an embedded flattened bell shaped core for controlling anterior bulging.
Figure 27:
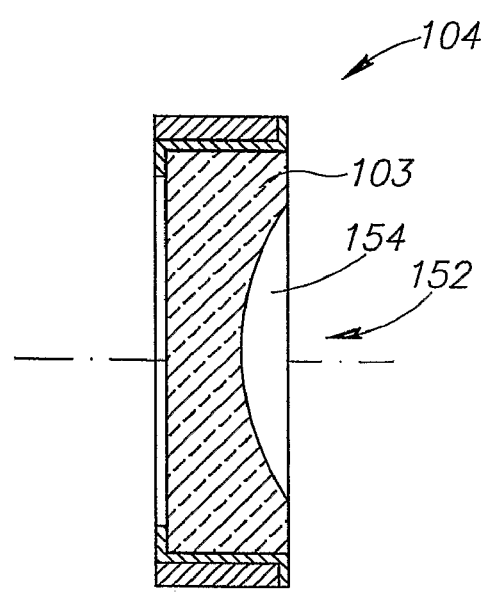
FIG. 27 is a longitudinal cross section of a haptics main body including an optical element with a rounded bulge control element in the form of a trailing rounded recess.
Figure 28:
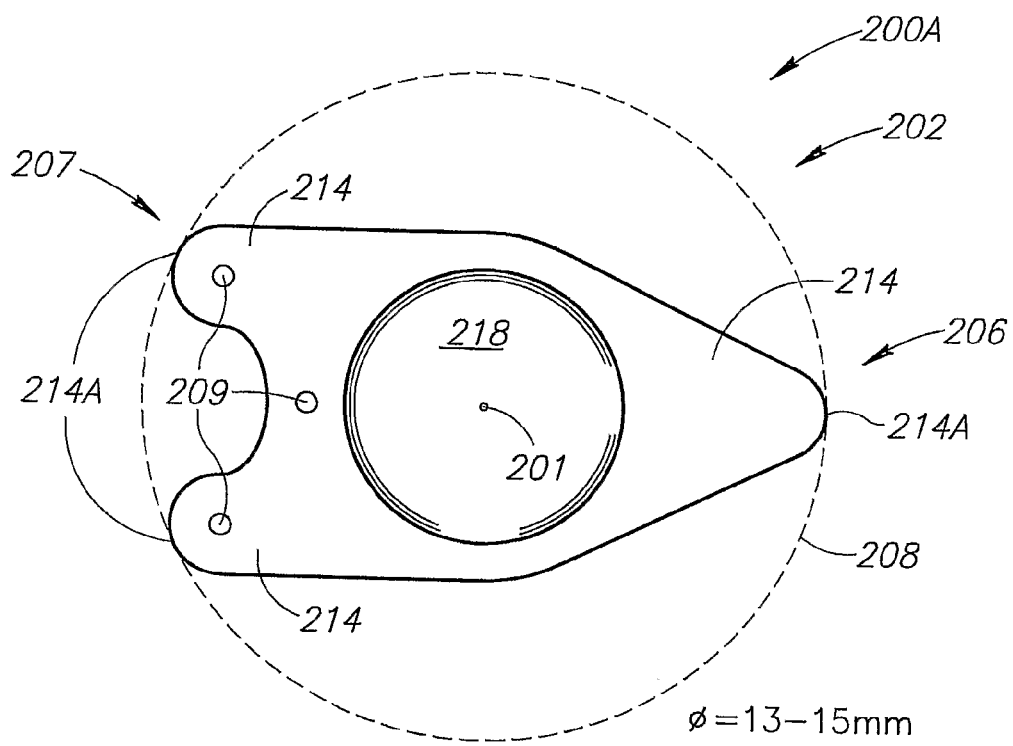
FIG. 28 is a plan view of an isosceles triangle shaped base member perpendicular to its longitudinal axis, the base member having a circular depression for use in conjunction with FIG. 3's unitary AIOL.
Figure 29:
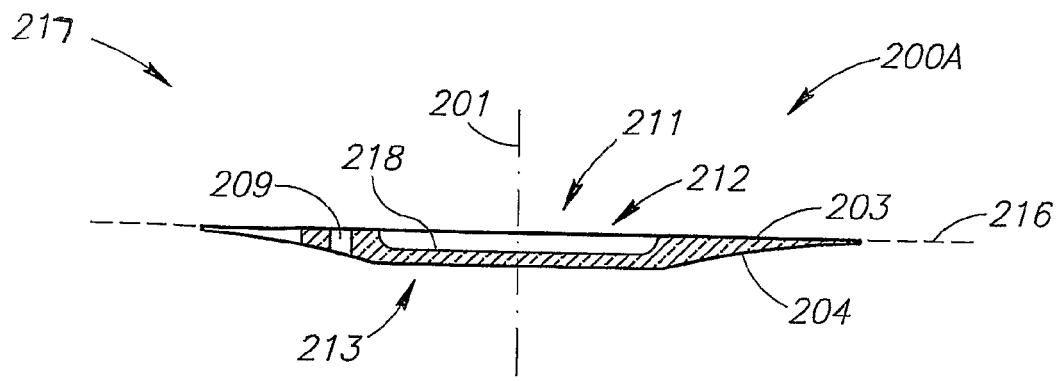
FIG. 29 is a longitudinal cross section of FIG. 28's base member having a posterior surface with a zero dioptric value.
Figure 30:
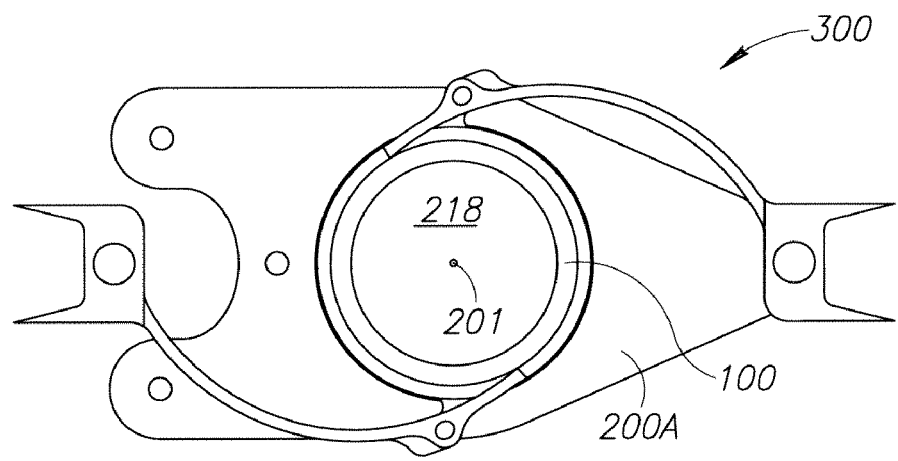
FIG. 30 is a plan view of an AIOL assembly including FIG. 3's unitary AIOL mounted on FIG. 28's base member.
Figure 31:
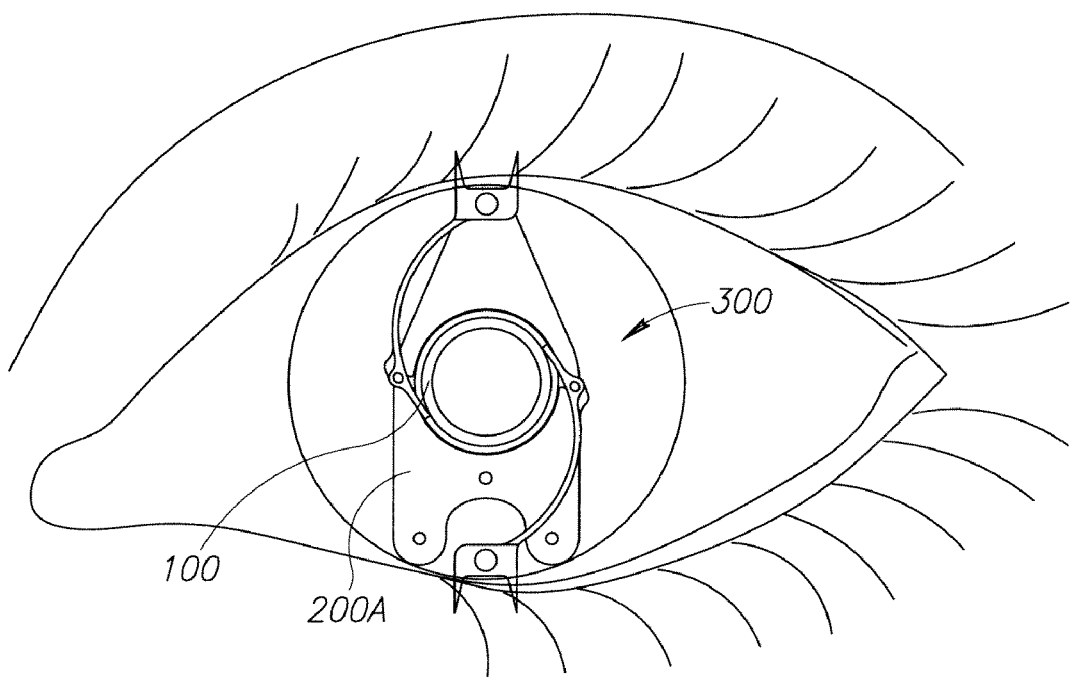
FIG. 31 is a front view of a human eye with FIG. 30's AIOL assembly implanted therein.
Figure 32:
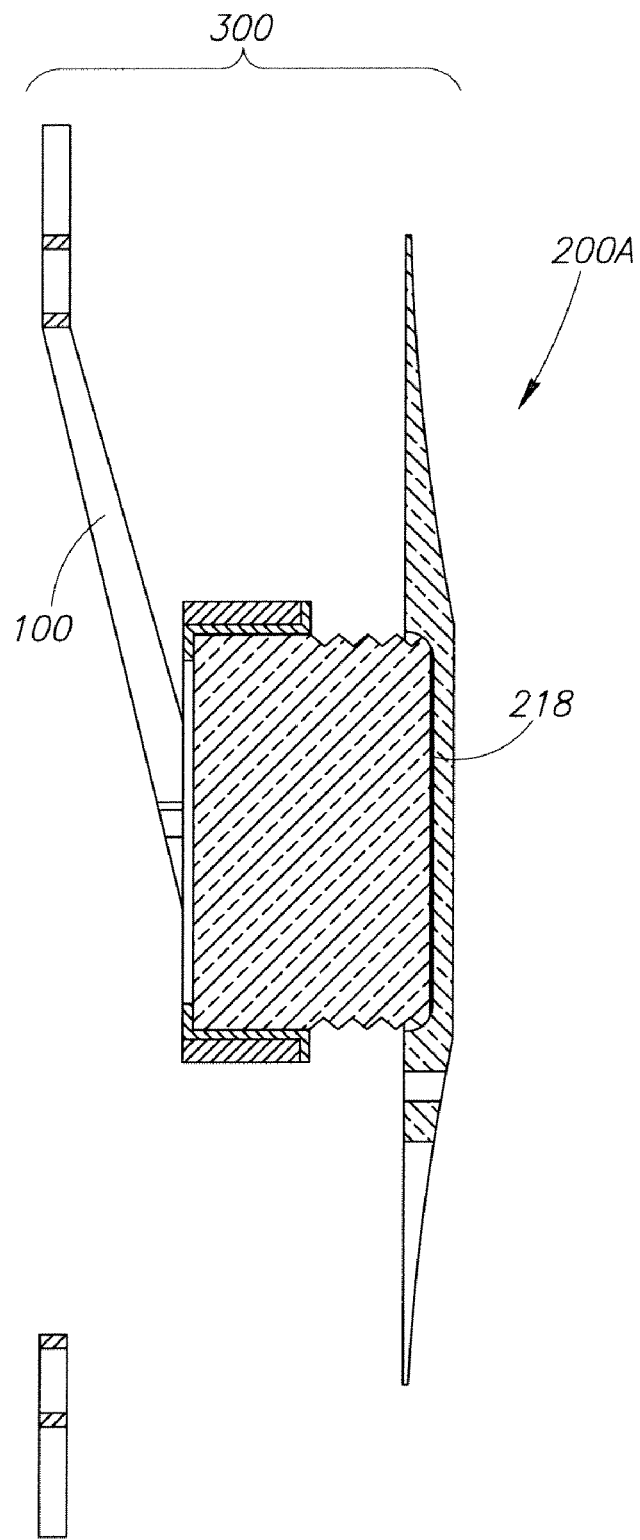
FIG. 32 is a longitudinal cross section of FIG. 30's AIOL assembly.

The optical elements 103 can be optionally additionally formed with a trailing bulge control element 152 for centering anterior bulging with respect to the longitudinal axis 101. The bulge control elements 152 typically have a height between about 0.4 mm to about 0.6 mm relative to an optical element's trailing surface 123. The bulge control elements 152 can be implemented as follows: First, the optical elements 103 can be provided with a biocompatible transparent silicon material core 153 having a hardness of typically several orders of magnitude greater than the major part of the optical member 103. Such cores 153 preferably have the same refractive index as the major part of the optical members 103 for avoiding aberrations at their interface. The cores 153 can have a spherical shape (see FIG. 25), a flattened bell shape (see FIG. 26), and the like. And second, a bulge control element 152 can be implemented as a rounded recess 154 for use with a base member having a complementary shaped core for snug insertion thereinto (see FIG. 27).

Purpose Designed Discrete Base Members

FIGS. 28 to 45 show discrete base members 200A-200I for use in AIOL assemblies 300 in conjunction with unitary AIOLs 100. The base members 200 have a longitudinal axis 201 intended to be co-axial with a unitary AIOL's longitudinal axis 101 and co-directional with a human eye's visual axis VA on implantation in a human eye 10. The base members 200 have an elongated substantially planar main body 202 with opposite major anterior and posterior surfaces 203 and 204. The base members 200 are preferably made from pliable biocompatible transparent material for enabling folding for insertion through a small incision into a human eye. Suitable materials include inter alia HydroxyEthylMethaAcrylate (HEMA), and the like.

The main bodies 202 have opposite leading and trailing ends 206 and 207 which define an imaginary circle 208 having an about 13 to 15 mm diameter which is sufficient to conform to the natural curvature of a human eye's capsular diaphragm and extend into substantially opposite sections of the human eye's ciliary sulcus 28. The trailing ends 207 are provided with preferably throughgoing manipulation bores 209 for enabling in situ manipulation, for example, by means of the aforesaid commonly owned WO 2008/023379's crooklike insertor tool (see WO 2008/023379's FIGS. 12 to 16). The main bodies 202 have a central piston member 211 with opposite leading and trailing working surfaces 212 and 213. The main bodies 202 have at least two lateral wings 214 extending radially from their central piston members 211 for forming the leading and trailing ends 206 and 207. The base members 200 preferably have an isosceles triangle shape in a plan view perpendicular to the longitudinal axis 201 in which case a single lateral wing 214 forms the leading end 206 and a pair of spaced apart lateral wings 214 form the trailing end 207 (see FIGS. 28 to 34). Alternatively, the base members 200 can have an elliptic shape in a plan view perpendicular to the longitudinal axis 201 such that a single lateral wing 214 forms each of their identical leading and trailing ends 206 and 207 (see FIGS. 35 and 36).

The base members 200 are generally planar in the absence of external forces thereon and their at least two lateral wings 214 define a horizontal plane 216 perpendicular to the longitudinal axis 201. The lateral wings 214 have a tapering thickness from a piston member 211 towards their extremities 214A on the imaginary circle 208 such that they are readily flexible on implantation in a human eye such that their extremities 214A are anterior of the horizontal plane 216 as they conform to the natural curvature of the human eye's capsular diaphragm 29.

Figure 41:
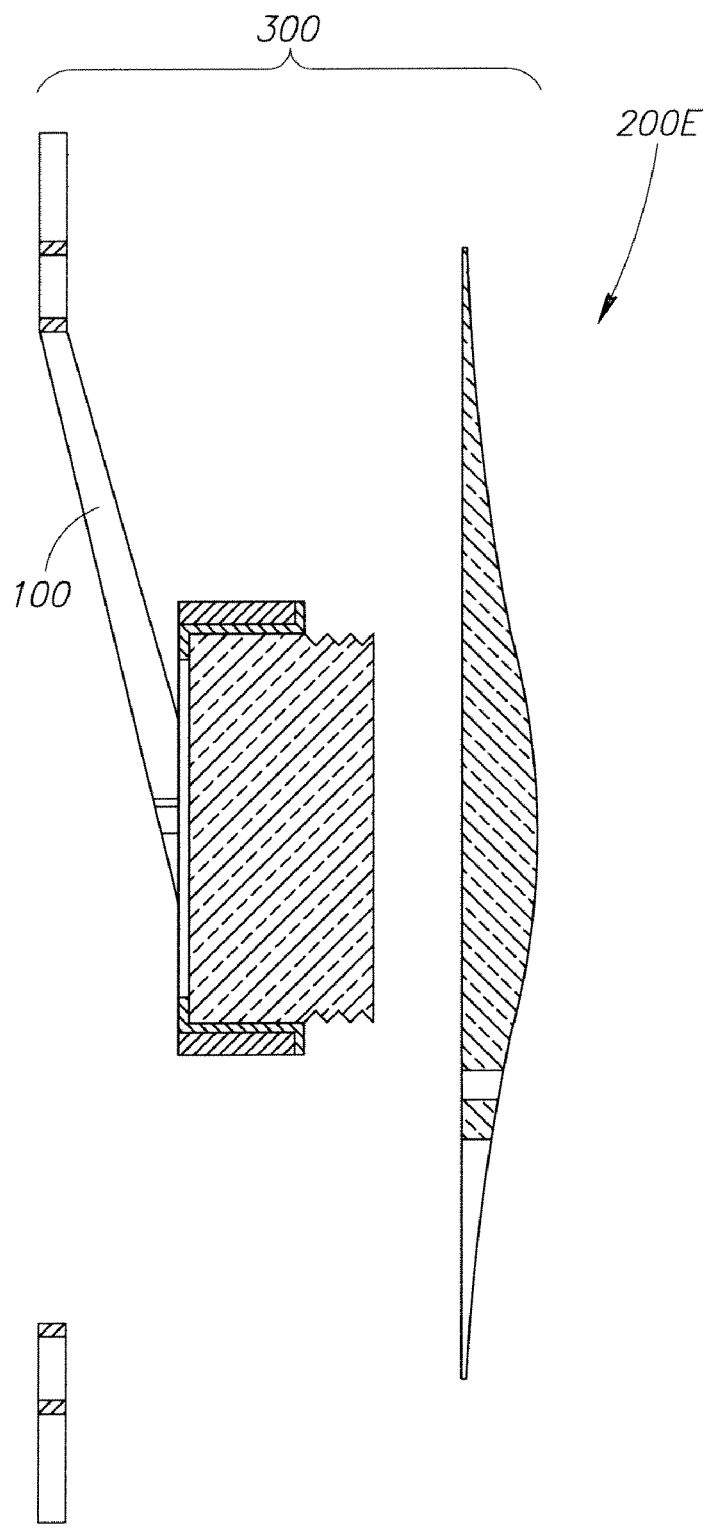
FIG. 41 is a longitudinal cross section of a FIG. 30's AIOL assembly including a base member having a flat anterior surface and a posterior surface with a positive dioptric value.
Figure 42:
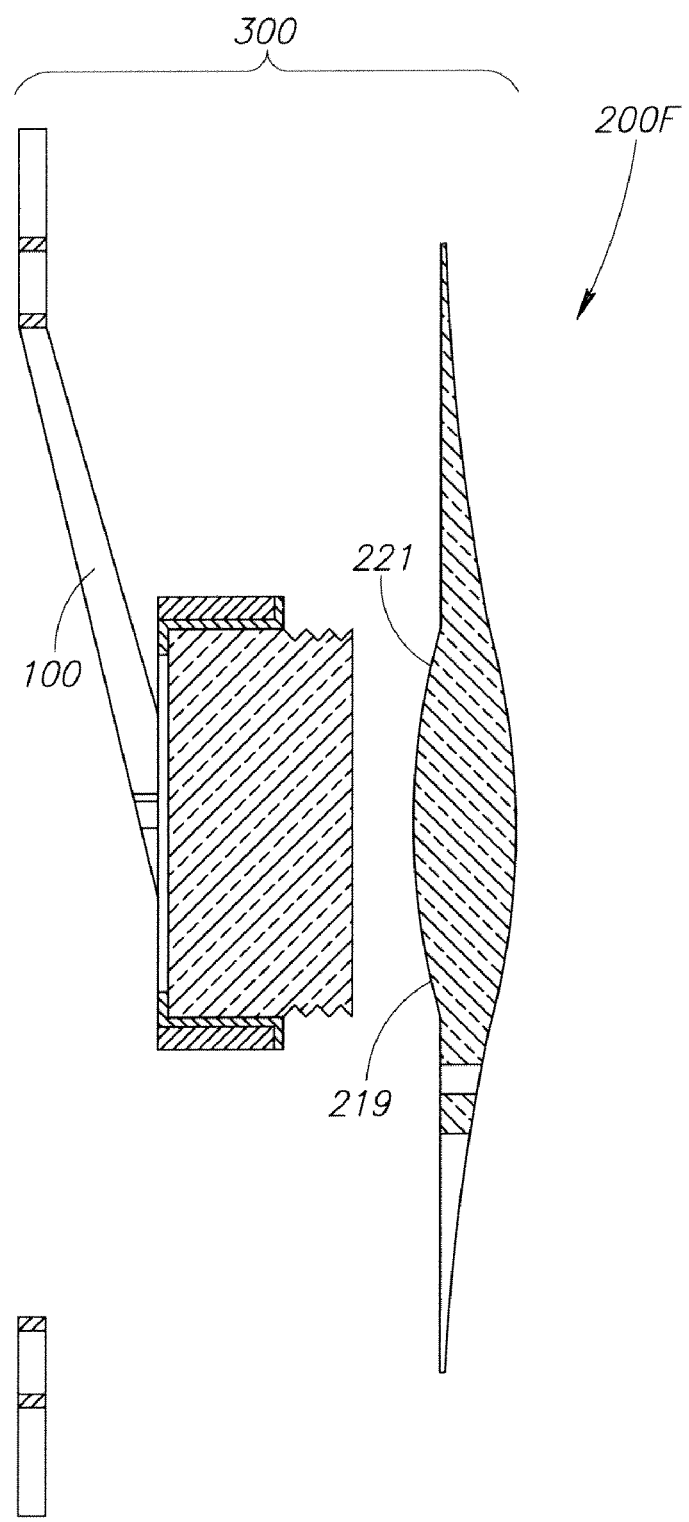
FIG. 42 is a longitudinal cross section of a FIG. 30's AIOL assembly including a base member having a leading working surface with an alignment element in the form of a rounded shape and a posterior surface with a positive dioptric value.

The base members 200 typically have leading working surfaces 212 formed with alignment elements 217 for co-axial alignment of a unitary AIOL 100 with a base member 200 but can have a flat anterior surface 203 (see FIG. 41). The alignment elements 217 have a complementary structure to a unitary AIOL's optical element's trailing surface 123. The base members 200A to 200D and 200H each have a leading working surface 212 formed with a circular depression 218 centered on their longitudinal axis 201 for use with unitary AIOLs 100 having an optical element 103 with a protruding trailing surface 123 with respect to its main body's trailing end face 108. The base members 200F, 200G and 200I each have a leading working surface 212 formed with a leading protrusion 219 centered on their longitudinal axis 201 for use with unitary AIOLs 100 having an optical element 103 with a trailing surface 123 flush with or recessed with respect to its main body's trailing end face 108. The leading protrusions 219 can be in the form of either a rounded shape 221 (see FIG. 42) or a disc-like step 222 (see FIG. 43).

Figure 43:
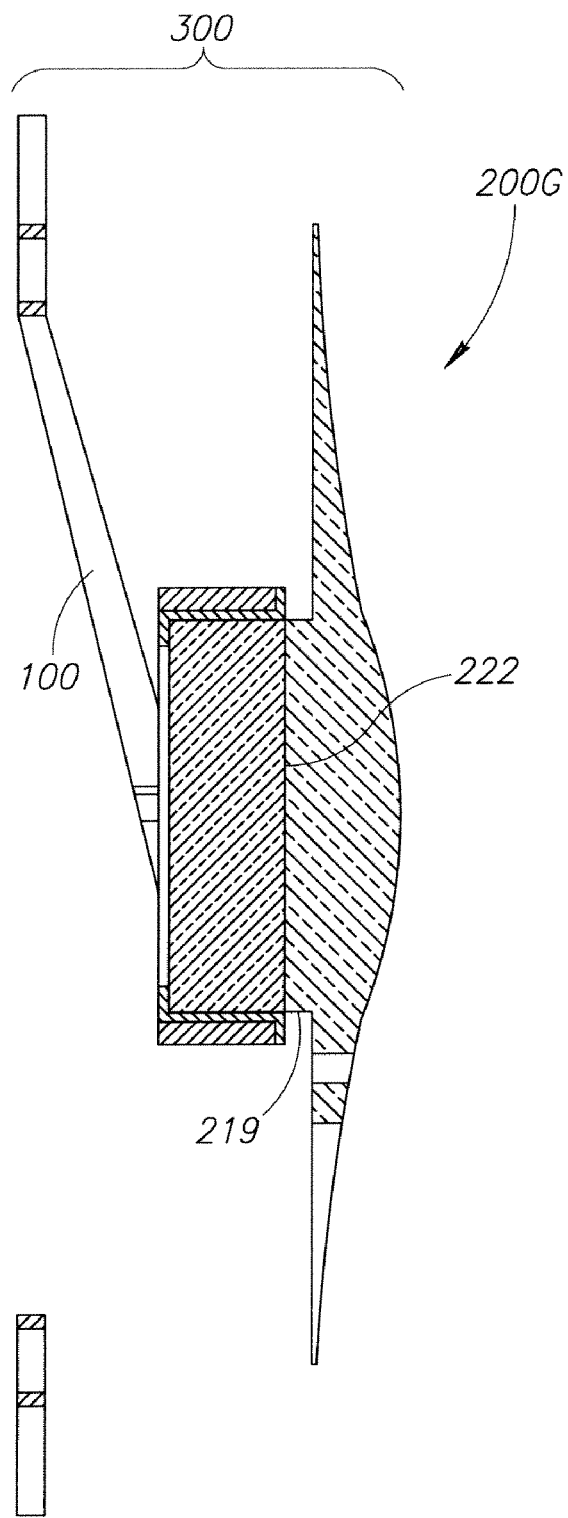
FIG. 43 is a longitudinal cross section of a unitary AIOL with FIG. 23's main body mounted on a base member with a leading working surface having an alignment element with a disc-like shape and a posterior surface with a positive dioptric value.
Figure 44:
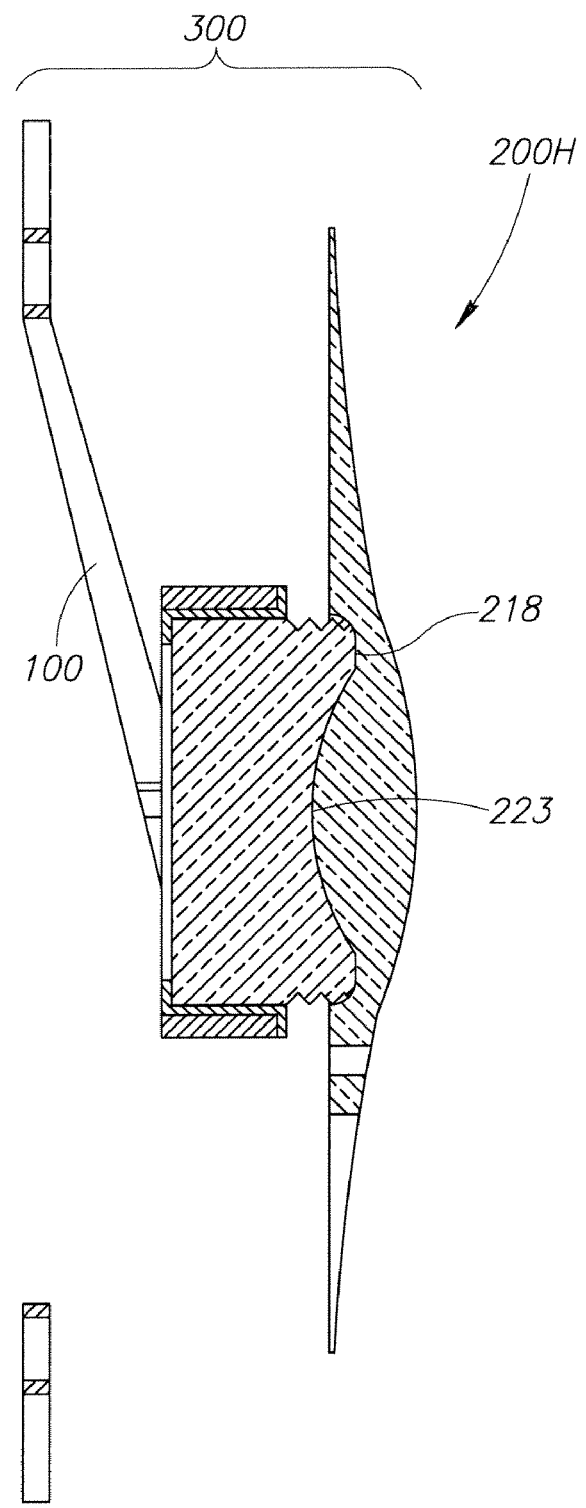
FIG. 44 is a longitudinal cross section showing FIG. 30's AIOL assembly including an unitary AIOL and a base member with complementary bulge control elements.
Figure 45:
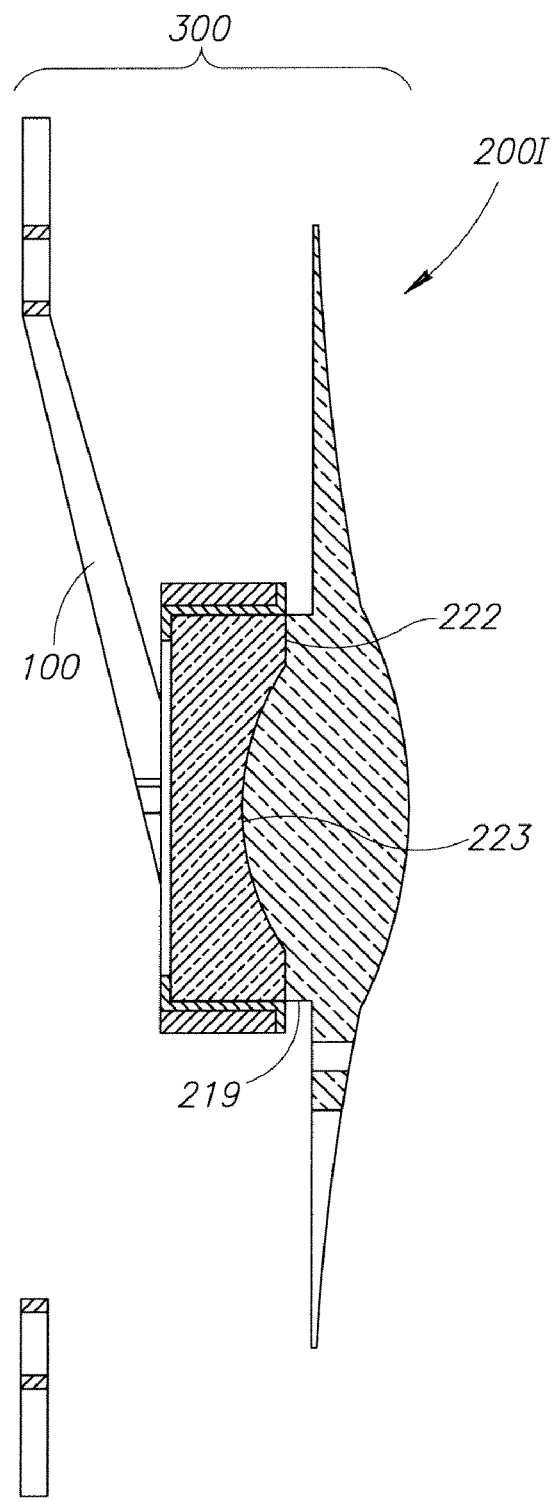
FIG. 45 is a longitudinal cross section showing FIG. 43's AIOL assembly including a unitary AIOL and a base member with complementary bulge control elements.

The alignment elements 218 and 219 can be formed with a bulge control core 223 for centering anterior bulging of optical elements 103 formed with bulge control elements 152 in the form of recesses 154 (see FIGS. 43 and 44).

The posterior surfaces 204 can be fashioned to meet different clinical conditions and/or optionally provide additional positive dioptric power if so required. The trailing working surfaces 213 can be formed with a trailing disc-like step 224 for protruding through a human eye's anterior capsule for ensuring that a posterior surface 204 simultaneously contacts a human eye's anterior capsule and its posterior capsule which are not directly overlying (see FIGS. 37 and 38). The base members 200A and 200C have posterior surfaces 204 with substantially zero dioptric power (see FIGS. 32 and 37). The base members 200D to 200I have posterior surfaces 204 with positive dioptric power (see FIGS. 39 to 45).

Figure 33:
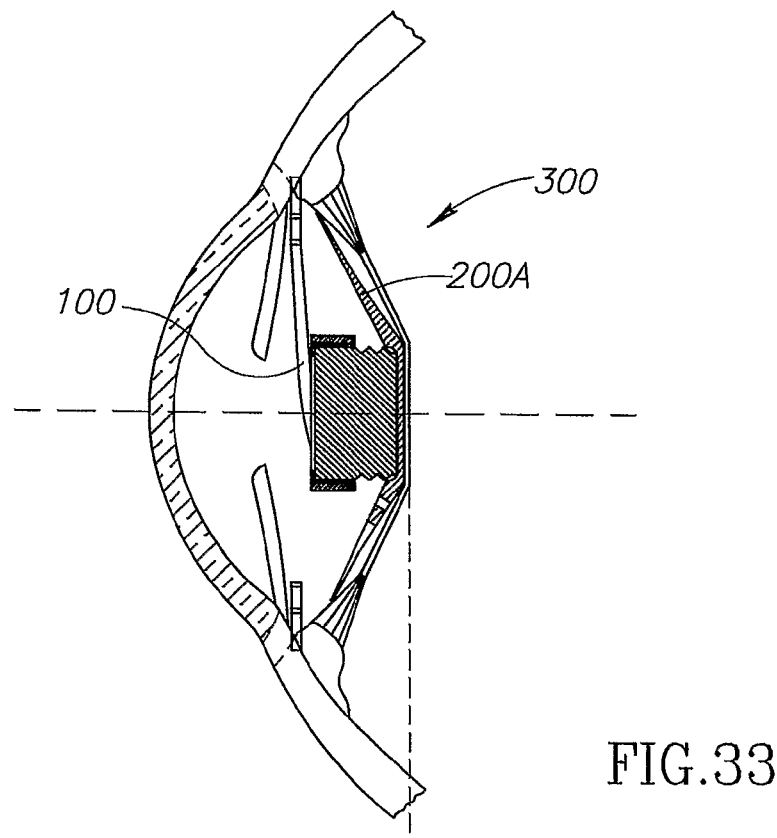
FIG. 33 is a longitudinal cross section of an anterior part of a human eye showing deployment of FIG. 30's AIOL assembly in an axial plane of the human body in the eye's contracted ciliary body state.
Figure 34:
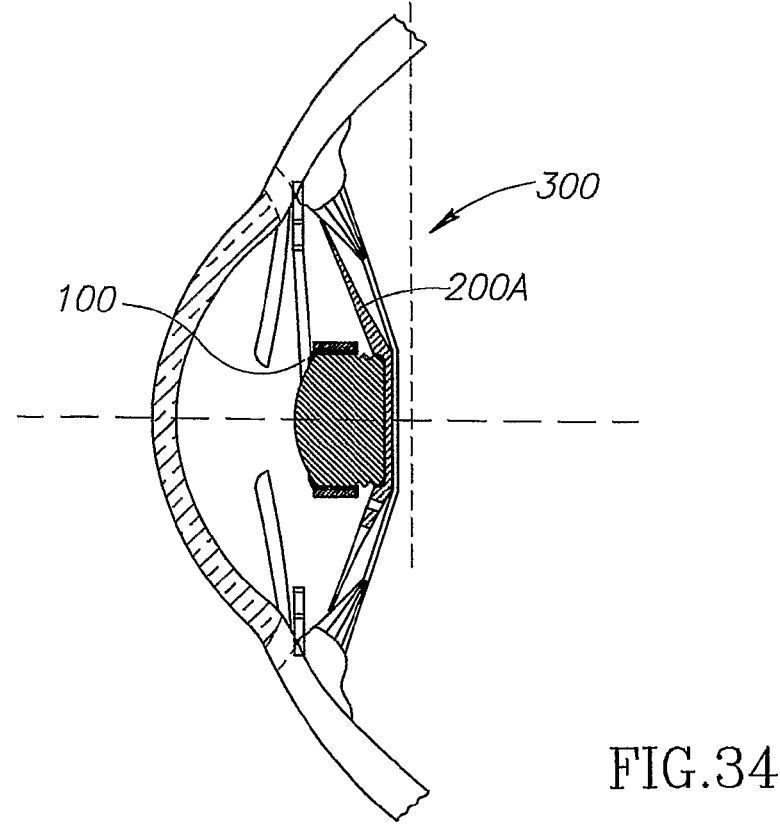
FIG. 34 is a longitudinal cross section of an anterior part of a human eye showing deployment of FIG. 30's AIOL assembly in an axial plane of the human body in the eye's relaxed ciliary body state.
Figure 35:
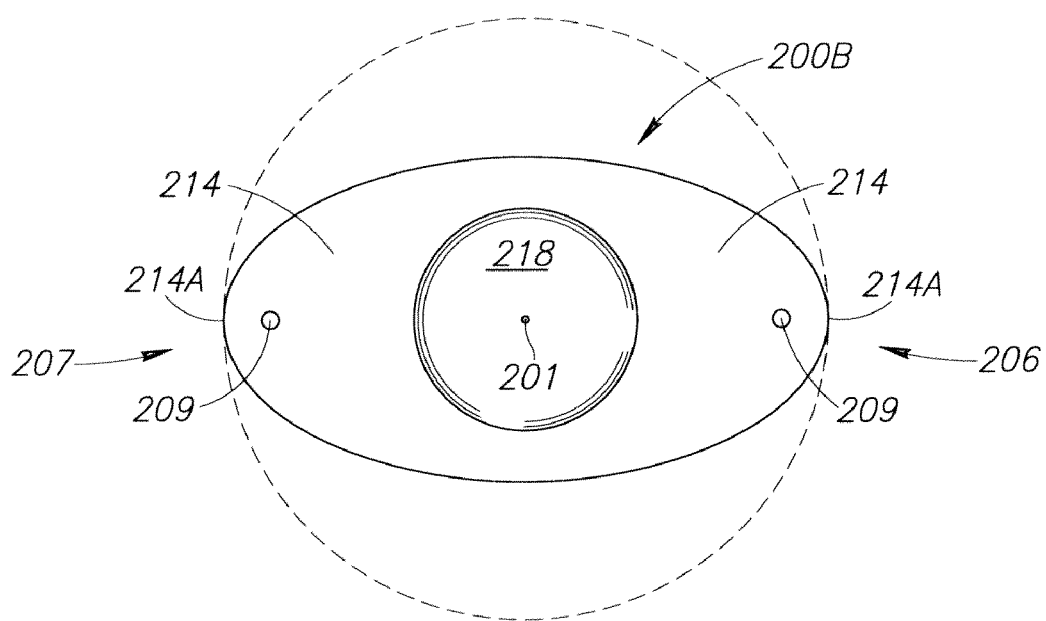
FIG. 35 is a plan view of an elliptic shaped base member perpendicular to its longitudinal axis, the base member having a circular depression for use in conjunction with FIG. 3's unitary AIOL.
Figure 36:
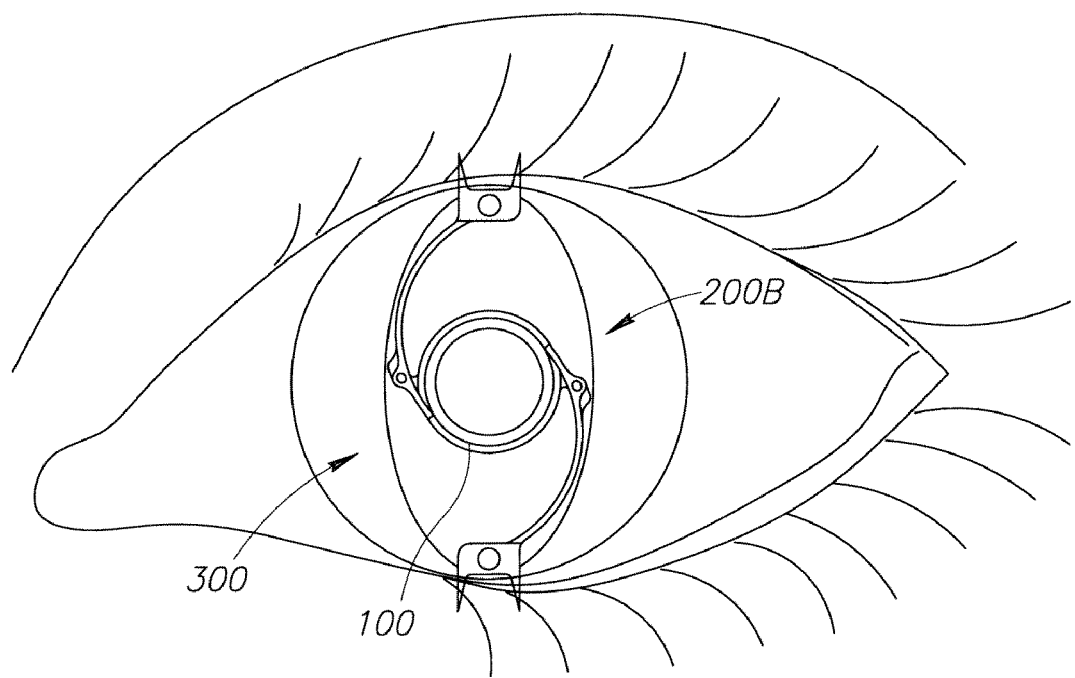
FIG. 36 is a front view of a human eye with FIG. 3's unitary AIOL mounted on FIG. 35's base member.
Figure 37:
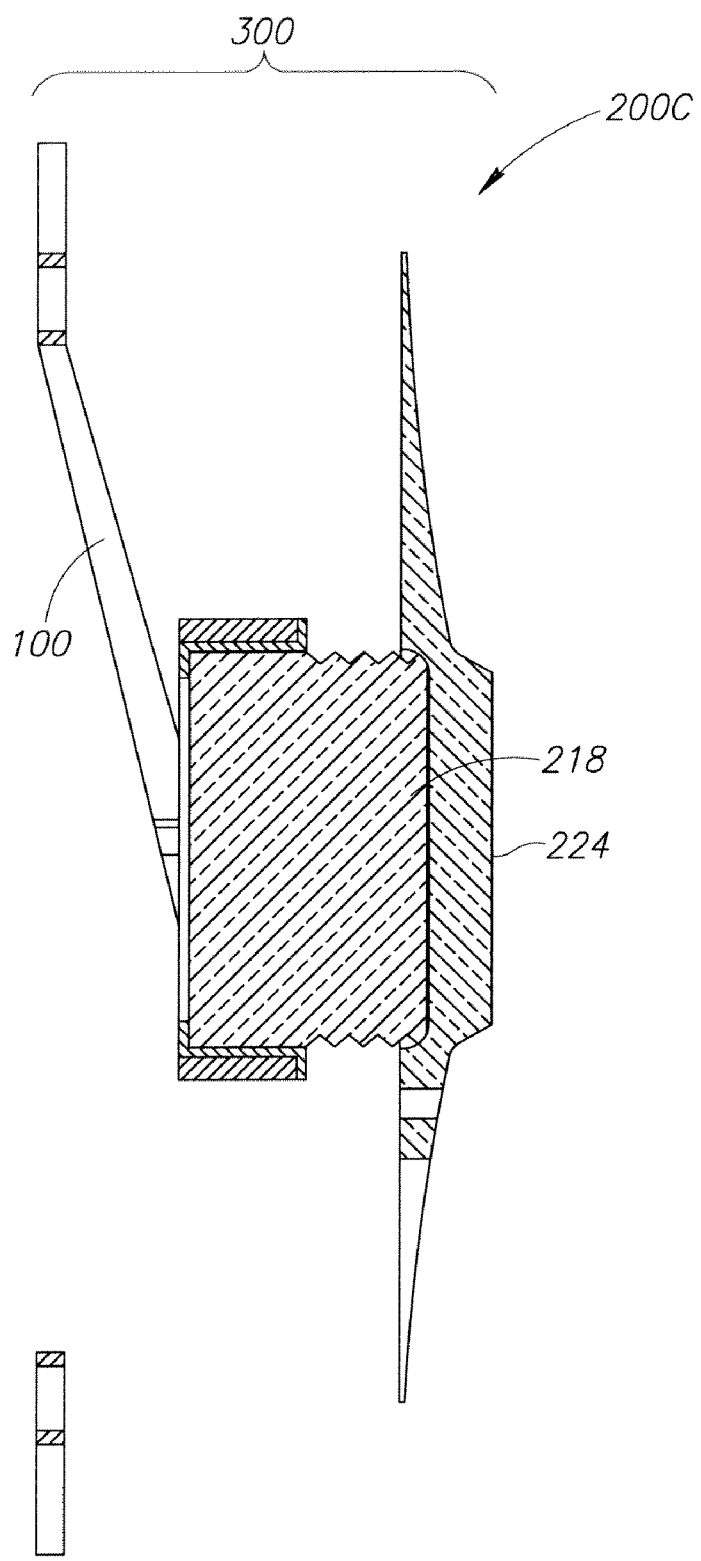
FIG. 37 is a longitudinal cross section of FIG. 30's AIOL assembly including a base member having a trailing working surface with a central disc-like step.
Figure 38:
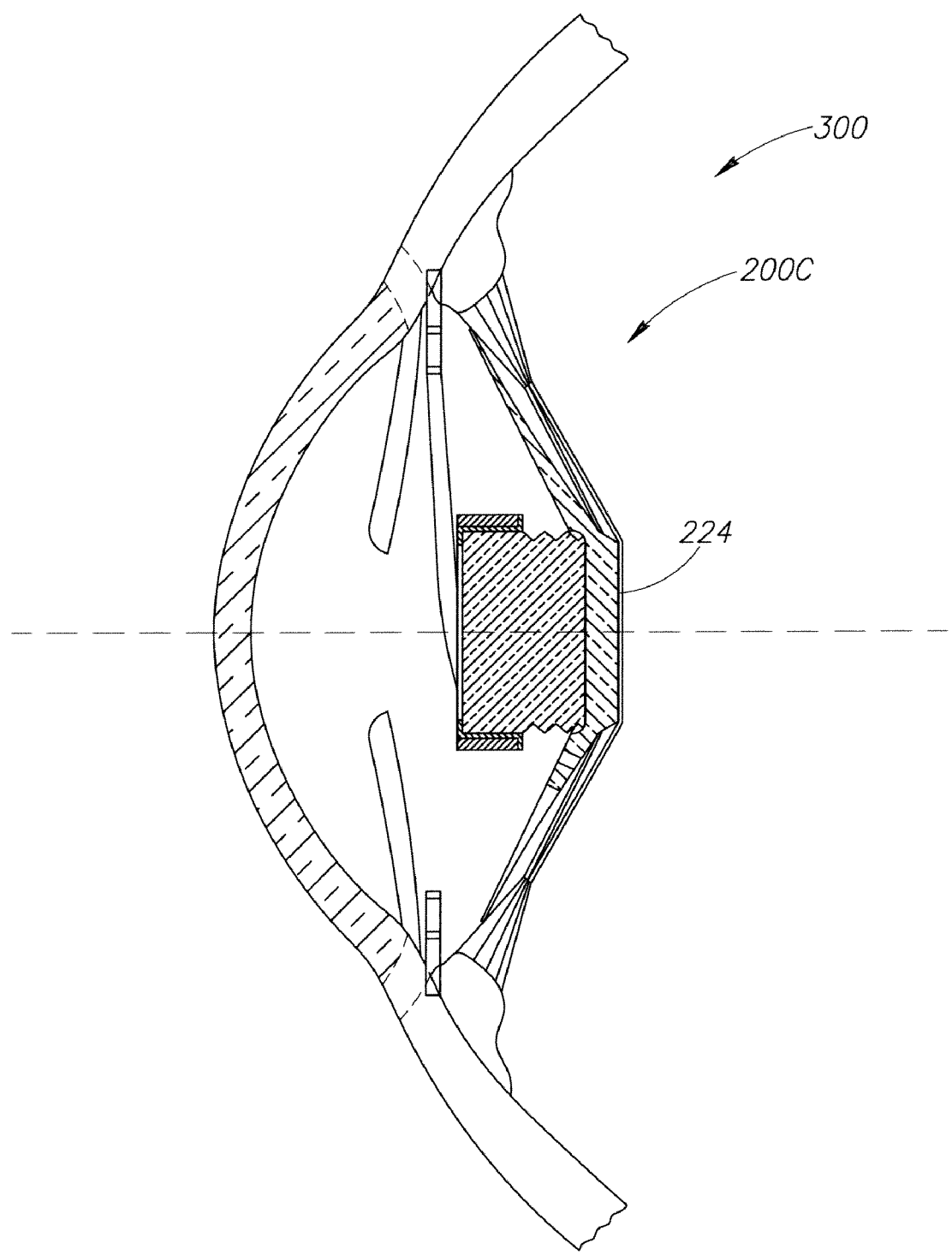
FIG. 38 is a longitudinal cross section of an anterior part of a human eye showing deployment of FIG. 37's AIOL assembly in an axial plane of the human body in its non-compressed state.
Figure 39:
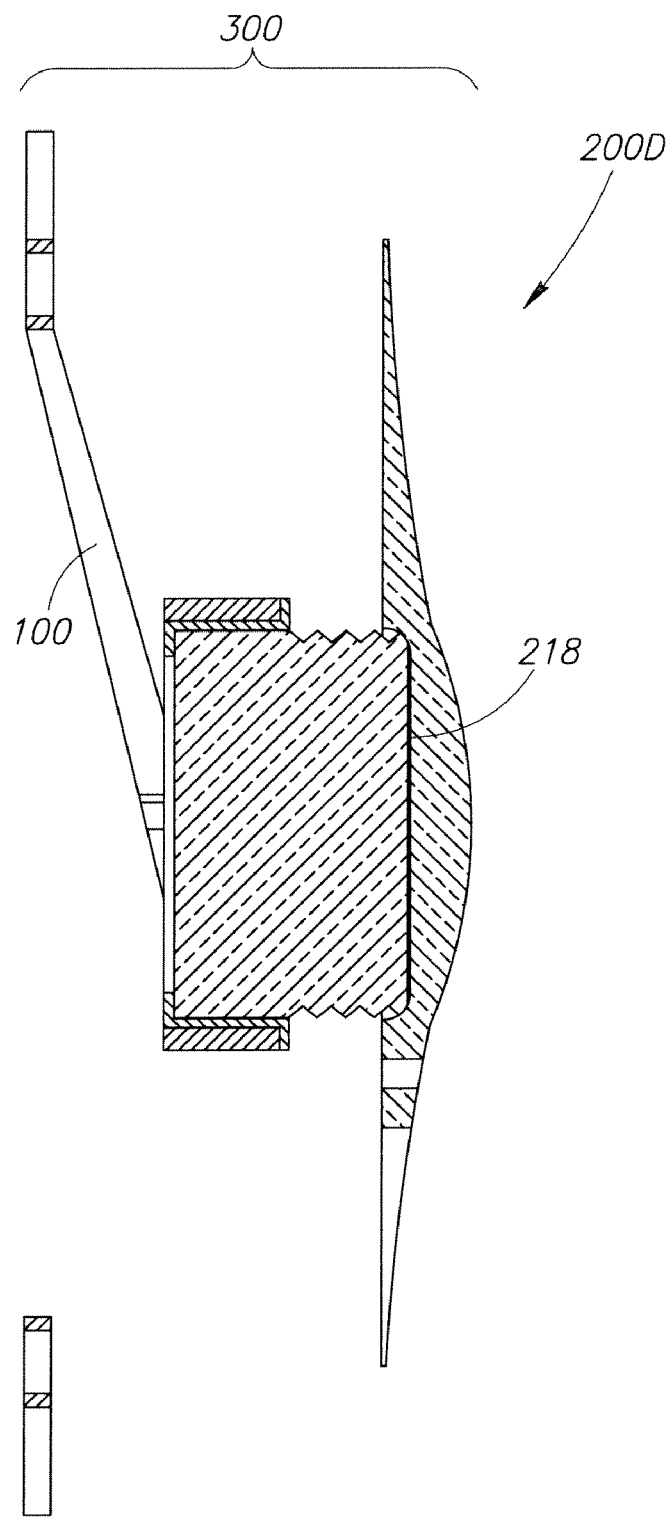
FIG. 39 is a longitudinal cross section of FIG. 30's AIOL assembly including a base member having a posterior surface with a positive dioptric value.
Figure 40:
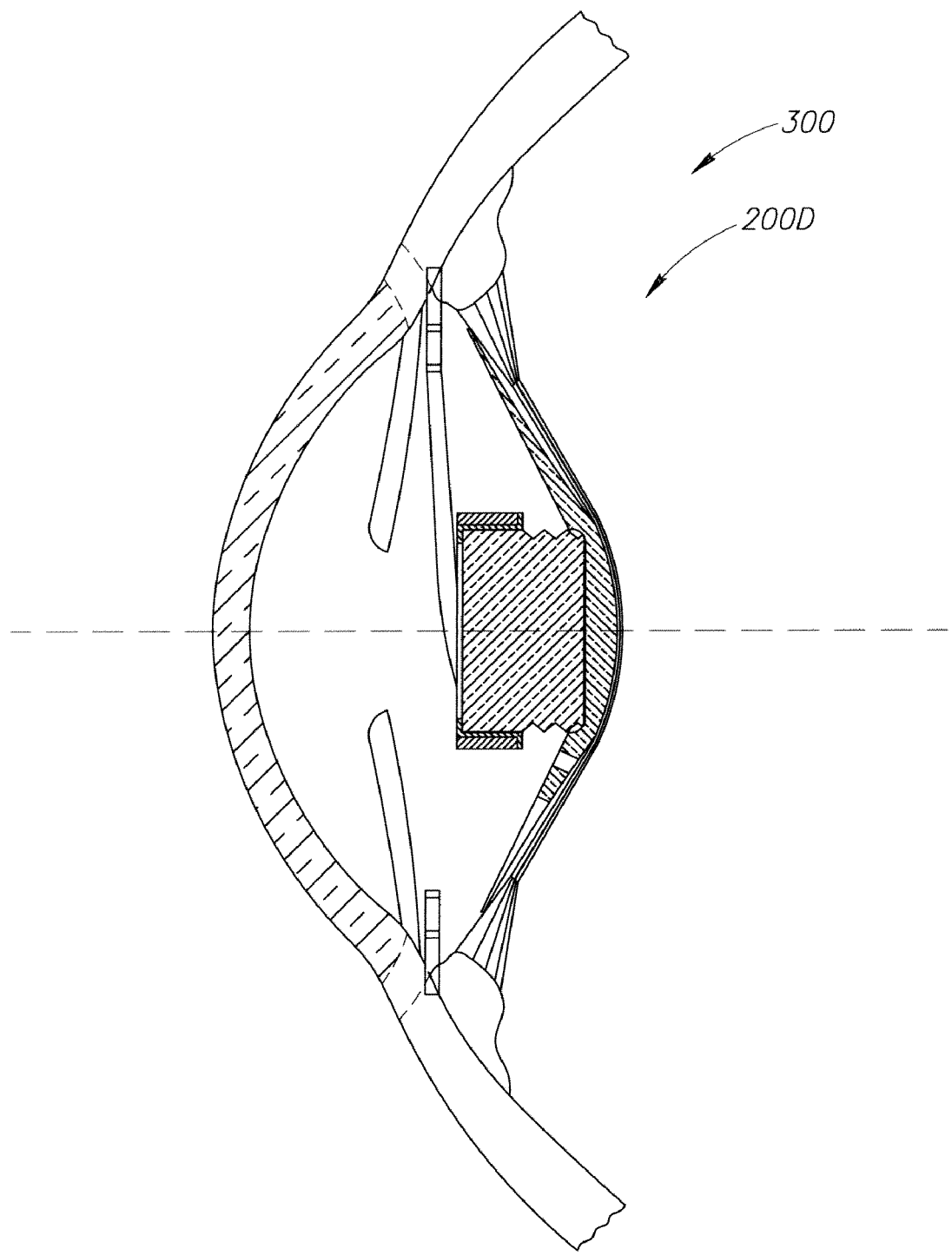
FIG. 40 is a longitudinal cross section of an anterior part of a human eye showing deployment of FIG. 39's AIOL assembly in an axial plane of the human body in its non-compressed state.

FIGS. 33 and 34 show implantation of an AIOL assembly 300 including FIG. 3's unitary AIOL 100 mounted on the base member 200A in a human eye 10 with the latter pre-tensioning against the eye's capsular diaphragm 29. FIG. 33 shows the AIOL assembly 300 in its non-compressed state in the eye's contracted ciliary body state for rendering a first preferably zero Diopter strength. FIG. 34 shows the AIOL 300 in its compressed state in the eye's relaxed ciliary body state for rendering a second Diopter strength different from the first Diopter strength.

While the invention has been described with respect to a limited number of embodiments, it will be appreciated that many variations, modifications, and other applications of the invention can be made within the scope of the appended claims.

The invention claimed is:

1. An accommodating intraocular lens (AIOL) system, comprising:
   (a) a unitary AIOL for self-anchoring implantation in a human eye having a visual axis, a sclera of tough connective tissue, an annular ciliary sulcus, and a sphincter-like ciliary body for tensioning a capsular diaphragm in an anterior direction along the visual axis on its relaxation from a contracted ciliary body state to a relaxed ciliary body state, the unitary AIOL having a longitudinal axis intended to be co-directional with the human eye's visual axis on implantation therein,
   said unitary AIOL comprising a generally disc-like resiliently elastically compressible shape memory optical element having a leading surface, an exposed trailing surface opposite said leading surface, and a peripheral surface with a trailing edge, said optical element having a continuously variable Diopter strength ranging between a first Diopter strength in a non-compressed state and a second Diopter strength different than said first Diopter strength in a compressed state on application of an axial compression force against said trailing surface by said discrete base member from a posterior direction along the unitary AIOL's longitudinal axis, the unitary AIOL further comprising a haptics system including a tubular haptics main body housing said optical element and including a leading inwardly directed annular flange and a trailing end face, said optical element's leading surface bulging through said annular flange on application of said axial compression force, said haptics main body having at least two elongated generally C-shaped haptics extending therefrom in opposite directions in a plane perpendicular to the unitary AIOL's longitudinal axis, each said haptics having at least one pointed puncturing member for penetrating the tough connective tissue of the human eye's sclera for self-anchoring implantation of the unitary AIOL in the human eye's annular ciliary sulcus at at least two spaced apart stationary anchor points for retaining the unitary AIOL in the human eye, said haptics each including a heat deformable region adjacent said haptics main body deformable on localized heating by an external energy source for enabling post implantation in situ selective axial displacement of said optical element along the human eye's visual axis relative to said at least two spaced apart stationary anchor points; and
   (b) a discrete base member which is previously implanted in the eye prior to implantation of the unitary AIOL, said discrete base member having a longitudinal axis intended to be co-directional with the human eye's visual axis on implantation thereof, said unitary AIOL being shaped and dimensioned so that said unitary AIOL, upon implantation, will receive axial compressive force from said discrete base member, wherein the capsular diaphragm acting, in use, pushes against the discrete base member to impart said axial compression force to said unitary AIOL.

2. The AIOL system of claim 1, wherein the discrete base member comprises an intraocular lens that was implanted in a previous procedure.

3. The AIOL system of claim 1, wherein the discrete base member comprises a discrete member that is implanted in the same procedure in which the unitary AIOL is implanted.

4. The AIOL system according to claim 1 wherein said haptics main body includes a tubular haptics ring with leading and trailing end faces and a tubular interposer disposed between said haptics ring and said optical element and wherein said interposer has a leading inwardly directed annular flange constituting said haptics main body's leading inwardly directed annular flange.

5. The AIOL system_according to claim 4 wherein said interposer has a trailing outwardly directed annular flange abutting against said haptics ring's trailing end face.

6. The AIOL system_according to claim 4 wherein said haptics ring is constituted by a single continuous tubular ring element.

7. The AIOL according to claim 4 wherein said haptics ring is constituted by a split ring arrangement including at least two ring elements.

8. The AIOL system_according to claim 7 wherein said split ring arrangement includes at least two interlocking ring elements.

9. The AIOL according to claim 7 wherein said split ring arrangement includes at least two hinged ring elements.

10. The AIOL system according to claim 1 wherein said haptics main body includes a tubular haptics ring integrally formed with a leading inwardly directed annular flange constituting said haptics main body's leading inwardly directed flange, and a trailing end face.

11. A method for implanting an accommodating intraocular lens (AIOL) for self anchoring implantation in a human eye having a visual axis, a sclera of tough connective tissue, an annular ciliary sulcus, and a sphincter-like ciliary body for tensioning a capsular diaphragm in an anterior direction along the visual axis on its relaxation from a contracted ciliary body state to a relaxed ciliary body state, said AIOL comprising a generally disc-like resiliently elastically compressible shape memory optical element having a leading surface, an exposed trailing surface opposite said leading surface, and a peripheral surface with a trailing edge, said optical element having a continuously variable Diopter strength ranging between a first Diopter strength in a non-compressed state and a second Diopter strength different than said first Diopter strength in a compressed state on application of an axial compression force against said trailing surface, the AIOL further comprising a haptics system including a tubular haptics main body housing said optical element and including a leading inwardly directed annular flange and a trailing end face, said optical element's leading surface bulging through said annular flange on application of said axial compression force, the AIOL having a longitudinal axis intended to be co-directional with the human eye's visual axis on implantation therein, said haptics main body having at least two elongated generally C-shaped haptics extending therefrom in opposite directions in a plane perpendicular to the unitary AIOL's longitudinal axis, each said haptic having at least one pointed puncturing member for penetrating the tough connective tissue of the human eye's sclera for self-anchoring implantation of the unitary AIOL in the human eye's annular ciliary sulcus at at least two spaced apart stationary anchor points for retaining the unitary AIOL in the human eye, said haptics each including a heat deformable region adjacent said haptics main body deformable on localized heating by an external energy source for enabling post implantation in situ selective axial displacement of said optical element along the human eye's visual axis relative to said at least two spaced apart stationary anchor points, the method comprising the steps of:
  (a) implanting said unitary AIOL in an eye in which a discrete base member has been previously implanted, said discrete base member having a longitudinal axis intended to be co-directional with the human eye's visual axis on implantation thereof; and
  (b) the step of implanting said unitary AIOL further comprising positioning the AIOL relative to the discrete base member to receive said axial compressive force from said discrete base member, wherein the capsular diaphragm, in use, pushes against the discrete base member to impart the axial compression force.

12. The method of claim 11, wherein the discrete base member comprises an intraocular lens that was implanted in a previous procedure.

13. The method of claim 11, wherein the discrete base member comprises a discrete member that is implanted in the same procedure in which the unitary AIOL is implanted.

* * * * *